(12) United States Patent
Berteau et al.

(10) Patent No.: US 10,214,718 B2
(45) Date of Patent: Feb. 26, 2019

(54) DISTRIBUTED PERFUSION BIOREACTOR SYSTEM FOR CONTINUOUS CULTURE OF BIOLOGICAL CELLS

(71) Applicants: Olivier Berteau, Reading, MA (US); Seongkyu Yoon, Walpole, MA (US); David Sergeant, Ecaussinnes (BE); Thierry Poskin, Obaix (BE)

(72) Inventors: Olivier Berteau, Reading, MA (US); Seongkyu Yoon, Walpole, MA (US); David Sergeant, Ecaussinnes (BE); Thierry Poskin, Obaix (BE)

(73) Assignees: University of Massachusetts, Boston, MA (US); APIcells Inc., Lowell, MA (US)

( * ) Notice: Subject to any disclaimer, the term of this patent is extended or adjusted under 35 U.S.C. 154(b) by 336 days.

(21) Appl. No.: 14/900,946

(22) PCT Filed: Jul. 1, 2014

(86) PCT No.: PCT/US2014/045155
§ 371 (c)(1),
(2) Date: Dec. 22, 2015

(87) PCT Pub. No.: WO2015/003012
PCT Pub. Date: Jan. 8, 2015

(65) Prior Publication Data
US 2016/0145563 A1    May 26, 2016

Related U.S. Application Data

(60) Provisional application No. 61/841,754, filed on Jul. 1, 2013.

(51) Int. Cl.
*C12M 1/00* (2006.01)
*C12M 1/34* (2006.01)
*C12M 1/36* (2006.01)

(52) U.S. Cl.
CPC ............ *C12M 41/48* (2013.01); *C12M 23/28* (2013.01); *C12M 23/40* (2013.01); *C12M 23/58* (2013.01); *C12M 29/10* (2013.01); *C12M 41/44* (2013.01)

(58) Field of Classification Search
CPC ...... C12M 41/48; C12M 23/28; C12M 23/40; C12M 23/58; C12M 29/10; C12M 41/44
See application file for complete search history.

(56) References Cited

U.S. PATENT DOCUMENTS

2004/0219659 A1    11/2004   Altman et al.
2011/0236932 A1     9/2011   Stobbe
(Continued)

FOREIGN PATENT DOCUMENTS

WO    2014/173745 A2    10/2014

OTHER PUBLICATIONS

Leader et al., Protein therapeutics: a summary and pharmacological classification. Nat Rev Drug Discov. Jan. 2008;7(1):21-39.
(Continued)

*Primary Examiner* — Gautam Prakash
*Assistant Examiner* — Lydia Edwards
(74) *Attorney, Agent, or Firm* — McCarter & English, LLP; Maneesh Gulati; Aaron P. Bumgarner

(57) ABSTRACT

Embodiments provide a distributed bioreactor system in which a plurality of modular bioreactors are operated in parallel to produce and maintain a biological cell culture. A central or nurse perfusion bioreactor produces and maintains a cell culture and transfers portions of the cell culture to a plurality of modular peripheral perfusion bioreactors, each of which produces and maintains the cell culture in turn. In order to prevent contamination and facilitate segregation of particular peripheral bioreactors, the distributed system is configured such that one-way fluid communication is estab-
(Continued)

lished from the central/nurse bioreactor to each of the peripheral bioreactors while maintaining fluid isolation among the peripheral bioreactors. Each modular peripheral bioreactor unit has a plug-and-play configuration and may be plugged into or otherwise coupled to the central/nurse bioreactor to scale up the overall size of the cell culture without requiring sterilization or redesign or reconfiguration of the system.

16 Claims, 24 Drawing Sheets

(56) References Cited

U.S. PATENT DOCUMENTS

2011/0294202 A1 12/2011 Wikswo et al.
2013/0005021 A1 1/2013 Bell et al.

OTHER PUBLICATIONS

Trampler et al., Acoustic cell filter for high density perfusion culture of hybridoma cells. Biotechnology (N Y). Mar. 1994;12(3):281-4.
International Search Report and Written Opinion for Application No. PCT/US2014/045155, dated Nov. 14, 2014. 11 pages.

DISTRIBUTED PERFUSION BIOREACTOR SYSTEM FOR CONTINUOUS CULTURE OF BIOLOGICAL CELLS

RELATED APPLICATIONS

The present application is a 35 U.S.C. § 371 national stage filing of International Application No. PCT/US2014/045155, filed Jul. 1, 2014, which claims priority to U.S. Provisional Application No. 61/841,754, filed Jul. 1, 2013. The entire contents of each of the foregoing applications are hereby incorporated by reference in their entirety.

BACKGROUND

Bioreactors support a biologically active environment for conducting a bio-chemical process involving biological organisms or biochemically active substances derived from such organisms. Bioreactor design is a complex engineering task requiring fine-tuning of bioreactor design and operational configuration to enable the cultured organisms to achieve their desired function. Before large-scale commercial manufacturing can be implemented, it is typically necessary to scale up a bioreactor during a process development stage. However, conventional scale-up techniques are fraught with technical challenges and financial risks.

Conventional techniques, for example, involve many steps of volume increases using different volumes of bioreactors. Control and test methods must be performed at each scale-up step as mass transfer of fluid tends to cause reduction in performance. Scale-up engineering involved in scaling up from the bench scale (i.e., a few liters) to the manufacturing scale (i.e., a couple of thousand liters) is complex, and it is difficult to ensure reproducibility of operation and performance at each scale-up step. Due to variability in operational and performance characteristics at each scale-up step, it is also challenging to satisfy regulatory and safety requirements using conventional scale-up techniques. Furthermore, in conventional scale-up, bioreactor components must be sterilized at each scale-up step.

SUMMARY

Embodiments provide a distributed bioreactor system (e.g., a distributed perfusion bioreactor system) in which a plurality of modular bioreactors (e.g., a plurality of modular perfusion bioreactors) are operated in parallel to produce and maintain a biological cell culture. A nurse or central perfused bioreactor produces and maintains a cell culture and transfers portions of the cell culture to a plurality of modular peripheral bioreactors (e.g., to a plurality of modular peripheral perfusion bioreactors), each of which produces and maintains the cell culture in turn. Each modular peripheral bioreactor unit has a plug-and-play configuration that may be plugged into or otherwise coupled to the central or nurse bioreactor to scale up the overall size of the cell culture without requiring sterilization of the whole bioreactor system. In order to prevent contamination and facilitate segregation of particular peripheral bioreactors, the distributed system is configured such that one-way fluid communication is established from the central or nurse bioreactor to each of the peripheral bioreactors while maintaining fluid isolation among the peripheral bioreactors. Exemplary distributed bioreactor systems may be configured to maintain the cell culture continuously for extended periods of time, including, but not limited to, more than a month, more than two months, more than three months, more than six months, and the like.

In accordance with one exemplary non-limiting embodiment, a distributed bioreactor system (e.g., a distributed perfusion bioreactor system) is provided for producing and maintaining a continuous biological cell culture. The distributed system includes a nurse or central perfused bioreactor configured to produce and maintain a cell culture, the nurse or central bioreactor coupled to a perfusion device. The distributed system also includes a plurality of peripheral bioreactors (e.g., a plurality of peripheral perfusion bioreactors) configured to produce and maintain a cell culture in parallel, each of the peripheral bioreactors, optionally coupled to a corresponding perfusion device. The distributed system also includes one or more control devices coupled to and configured to control the perfusion devices associated with the central/nurse and peripheral bioreactors (and to control fluid exchange between bioreactors within the system), and a multi-way manifold coupled to the central/nurse perfusion bioreactor. The distributed system further includes a plurality of one-way fluid conduits configured to provide fluid communication from the central/nurse perfused bioreactor to the plurality of peripheral bioreactors, each one-way fluid conduit coupling the central/nurse bioreactor to one of the peripheral bioreactors using the multi-way manifold. Configuration of the multi-way manifold and the one-way fluid conduits enables transfer of the cell culture from the central/nurse bioreactor to at least two of the peripheral bioreactors and maintains fluid isolation among each of the peripheral bioreactors.

In accordance with another exemplary non-limiting embodiment, a method is provided for assembling a distributed bioreactor system (e.g., a distributed perfusion bioreactor system) for producing and maintaining a biological cell culture. The method includes receiving a central or nurse perfused bioreactor and receiving a plurality of sterile modular bioreactor units, each modular unit comprising a peripheral bioreactor (e.g., a peripheral perfusion bioreactor). The method also includes coupling a multi-way manifold to an outlet port of the central/nurse bioreactor and coupling each of the modular units to the multi-way manifold using a one-way fluid conduit for providing fluid communication from the central/nurse bioreactor to the modular unit. Configuration of the multi-way manifold and the one-way fluid conduits enables transfer of a cell culture from the central/nurse bioreactor to at least two of the peripheral bioreactors and maintains fluid isolation among each of the peripheral bioreactors. The method further includes coupling a plurality of perfusion devices to the central/nurse bioreactor and the peripheral bioreactors and providing one or more control devices configured to control the perfusion devices during production and maintenance of the cell culture.

In accordance with another exemplary non-limiting embodiment, a computer-implemented method is executed on a bioreactor control computing device for controlling production and maintenance of a biological cell culture in a first perfused bioreactor coupled to a first perfusion device. The method includes detecting a cell density corresponding to the cell culture using a suitable cell density (e.g., optical capacitance, picture-based or other) probe and determining a cell concentration of the cell culture based on the probe signal. The method also includes upon determining that the cell concentration satisfies a predefined cell concentration threshold, automatically changing an operational state of the first bioreactor.

In accordance with another exemplary non-limiting embodiment, a method is provided for producing and maintaining a biological cell culture in a first perfused bioreactor. The method includes, upon inoculation of the cell culture in the first bioreactor, shutting off a medium inlet port and a medium outlet port of the first bioreactor to maintain the cell culture in the first bioreactor at a substantially constant volume during a batch state. The method also includes, upon determining that a cell concentration of the cell culture in the first bioreactor has reached a first predefined cell concentration threshold, opening the medium inlet port to introduce a cell growth medium into the first bioreactor to maintain the cell concentration substantially at the first cell concentration threshold during a fed-batch state. The method also includes, upon determining that a volume of the cell culture in the first bioreactor has reached a first predefined volume threshold, opening the medium inlet port and the medium outlet port and controlling the first perfusion device to introduce the cell growth medium into the first bioreactor and to release spent cell growth medium from the first bioreactor while maintaining the volume of the cell culture substantially at the first volume threshold during a perfused batch state. The method also includes, upon determining that a cell concentration of the cell culture in the first bioreactor has reached a second predefined cell concentration threshold, opening the medium inlet port and controlling the first perfusion device to introduce the cell growth medium into the first bioreactor and to release spent cell growth medium from the first bioreactor while maintaining the cell concentration substantially at the second cell concentration threshold during a perfused fed-batch state. The method further includes, upon determining that a volume of the cell culture in the first bioreactor has reached a second predefined volume threshold, opening the medium inlet port and the medium outlet port and controlling the first perfusion device to continually introduce the cell growth medium into the first bioreactor and to continually release spent medium from the first bioreactor to maintain a volume of the cell culture substantially at the second volume threshold while the cell concentration is kept at the second cell concentration threshold.

It is noted that by an appropriate choice of the first and second predefined cell concentration thresholds and/or the first and second predefined volume thresholds, the culture modes can be used or skipped (e.g., if the first concentration threshold is equal to the second concentration, the perfused batch mode will be skipped and the system will switch from fed-batch to perfused fed-batch).

Exemplary embodiments further provide one or more non-transitory computer-readable media having encoded thereon one or more computer-executable instructions that, when executed on a bioreactor control computing system or device, perform any of the methods described herein.

BRIEF DESCRIPTION OF THE DRAWINGS

The foregoing and other objects, aspects, features, and advantages of exemplary embodiments will become more apparent and may be better understood by referring to the following description taken in conjunction with the accompanying drawings, in which.

Figure 1:
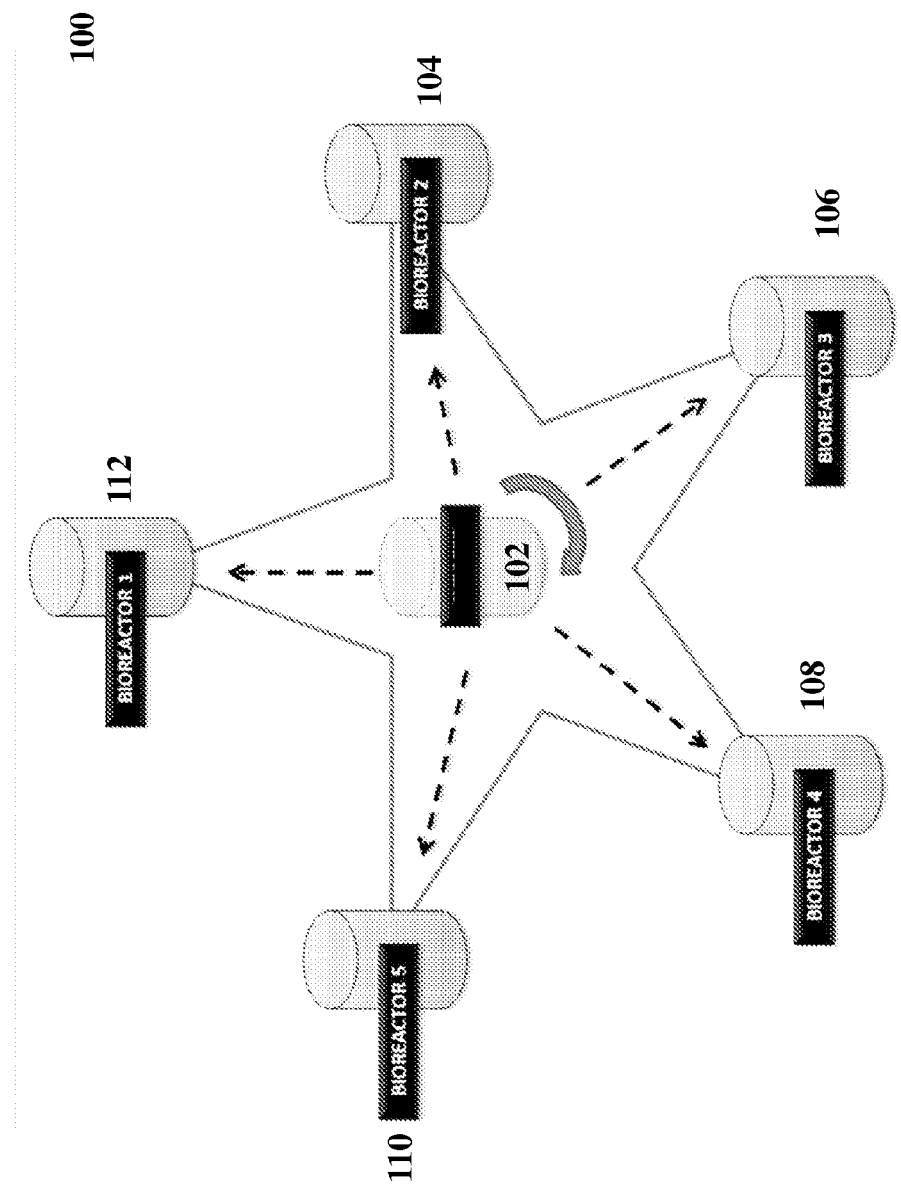
FIG. 1 is a schematic illustrating an exemplary distributed perfusion bioreactor system including a central bioreactor and a plurality of peripheral bioreactors.

The accompanying drawings are not intended to be drawn to scale.

DETAILED DESCRIPTION

Exemplary embodiments provide an in-vitro, continuous, universal and modular system for production of cultured cells based on a scale-free model to respond to the requirements of the pharmaceutical and biotechnology industries. Exemplary embodiments enable automatic and real-time control of the perfusion process so that the process is able to run for extended periods of time (e.g., several weeks to several months) with little or no human intervention, thereby improving production control, reducing volumes required and enabling more precise control of the time and performance of each bioreactor as well as the whole production plant.

In an exemplary distributed bioreactor system (e.g., distributed perfusion bioreactor system), a plurality of modular bioreactors (e.g., modular perfusion bioreactors) are operated in parallel to produce and maintain a biological cell culture. A central or nurse perfused bioreactor produces and maintains a cell culture and transfers portions of the cell culture to a plurality of modular peripheral bioreactors (e.g., modular peripheral perfusion/perfused bioreactors), each of which produces and maintains the cell culture in turn. In order to prevent contamination and facilitate segregation of particular peripheral bioreactors, the distributed system is configured such that one-way fluid communication is established from the central/nurse bioreactor to each of the peripheral bioreactors while maintaining fluid isolation among the peripheral bioreactors.

Each modular peripheral bioreactor unit has a plug-and-play configuration that may be plugged into or otherwise coupled to the nurse or central bioreactor to scale up the overall size of the cell culture without requiring sterilization. That is, additional peripheral modules may be "copied and pasted" into the bioreactor system to scale up the overall culture volume for mass production. The modularity of the peripheral bioreactors enables a scale-up free design of an exemplary bioreactor system that avoids the disadvantages of a conventional scale-up technique. For example, the modularity of the peripheral bioreactors facilitates additional modular units to be coupled to the nurse or central bioreactor easily and efficiently, without sterilizing, retesting or reconfiguring the entire system, in order to scale up the overall cell culture volume of the system. Another significant advantage of the exemplary system is that there is no need for reconfiguring the operation of the system to accommodate the differing conditions and operations in larger bioreactors.

The same bioreactor design may thereby be used throughout the distributed bioreactor system at one or more different scales, e.g., bioreactor volumes of about 5, 20 and 200 L. For example, the same bioreactor components and model may be used for the process development (PD) stage and the manufacturing stage of the operation.

The modularity of the peripheral bioreactors also enables detection of process deviations and contamination, and easy and efficient segregation or restart of an affected peripheral bioreactor branch without disrupting the entire system.

I. Definition of Terms

Certain terms are defined in this section to facilitate understanding of exemplary embodiments.

The prefix "cyto," as used herein, refers to a cell or cells.

The terms "cell density," "viable cell density" and "cell concentration," as used herein, refer interchangeably to the number of metabolically active cells per unit volume of a cell culture.

The term "cell bank," as used herein, refers to a storage of biological cells.

The term "bioreactor," as used herein, refers to any suitable vessel or other means of producing and maintaining a biological cell culture including, but not limited to, a perfusion/perfused bioreactor.

The terms "perfusion" or "cyto-perfusion," as used herein, refer to a fermentation or cell culture process used to produce a targeted biological product, e.g., an antibody or recombinant protein, in which a high concentration of cells within a sterile chamber receive fresh growth medium continually as the spent medium which may contain a targeted biological product that is harvested.

The term "batch state," as used herein, refers to a bioreactor operational state in which the cell concentration of the cell culture increases while the volume is maintained at a substantially constant level.

The term "fed-batch state," as used herein, refers to a bioreactor operational state in which the volume of the biological cell culture is adjusted by introducing a cell growth medium into the bioreactor.

The term "perfused batch state," as used herein, refers to a bioreactor operational state in which a perfusion device is operated to retain cells within the bioreactor while a cell growth medium is introduced into the bioreactor and a spent medium is harvested from the bioreactor, while maintaining the volume of the cell culture at a substantially constant level.

The term "perfused fed-batch state," as used herein, refers to a bioreactor operational state in which a perfusion device is operated to retain cells within the bioreactor while a cell growth medium is introduced into the bioreactor and a spent medium is harvested from the bioreactor, while maintaining the cell concentration at a substantially constant level.

The term "cytostat state," as used herein, refers to a bioreactor operational state in which a perfusion device is operated to retain cells within the bioreactor while a cell growth medium is introduced into the bioreactor and a spent medium is harvested from the bioreactor, while maintaining the volume of the biological cell culture at a substantially constant level (in the case when a bleeding is allowed, the cell concentration can be maintained at a substantially constant level in the same time).

The term "computer-readable medium," as used herein, refers to a non-transitory storage hardware, non-transitory storage device or non-transitory computer system memory that may be accessed by a controller, a microcontroller, a computational system or a module of a computational system to encode thereon computer-executable instructions or software programs. The "computer-readable medium" may be accessed by a computational system or a module of a computational system to retrieve and/or execute the computer-executable instructions or software programs encoded on the medium. The non-transitory computer-readable media may include, but are not limited to, one or more types of hardware memory, non-transitory tangible media (for example, one or more magnetic storage disks, one or more optical disks, one or more USB flash drives), computer system memory or random access memory (such as, DRAM, SRAM, EDO RAM) and the like.

The terms "equal" and "substantially equal," as used herein, refer interchangeably, in a broad lay sense, to exact equality or approximate equality within some tolerance.

The terms "similar" and "substantially similar," as used herein, refer interchangeably, in a broad lay sense, to exact sameness or approximate similarity within some tolerance.

The terms "couple," "coupled" and "coupling," as used herein, refer to a direct or indirect connection among two or more components. For example, a first component may be coupled to a second component directly or through one or more intermediate components.

II. Exemplary Distributed Bioreactor System

An exemplary distributed bioreactor system (e.g., distributed perfusion bioreactor system) includes a plurality of modular bioreactors (e.g., plurality of modular perfusion bioreactors) that are operated automatically and controlled in real-time to produce and maintain a biological cell culture. In some cases, all of the bioreactors in the system may be running continuously, separately and simultaneously, with a control device automatically and remotely controlling the operation of each bioreactor. In an exemplary distributed system, a bioreactor (referred to herein as a "nurse" or a "central" bioreactor) produces and maintains a cell culture and transfers portions of the cell culture to a plurality of sterile modular (e.g., perfusion) bioreactors (referred to herein as "peripheral" bioreactors), each of which produces and maintains the cell culture in turn. Each modular peripheral bioreactor unit has a plug-and-play configuration that may be plugged into or otherwise coupled to the nurse/central bioreactor without requiring sterilization. At any given time, the different bioreactors in the distributed system may be operating in the same or in different operational states. Nonetheless, the parallel operation of the nurse/central and peripheral bioreactors enables a large volume of the cell culture to be produced and maintained in the system. Exemplary distributed bioreactor systems may be configured to maintain the cell culture continuously for extended periods of time, including, but not limited to, more than a month, more than two months, more than three months, more than six months, and the like.

FIG. 1 is a schematic illustrating an exemplary distributed bioreactor system 100 (e.g., distributed perfusion bioreactor system 100) including a central/nurse bioreactor 102 and five peripheral bioreactors 104, 106, 108, 110, 112 (e.g., five peripheral perfusion bioreactors) coupled to the central/nurse bioreactor 102. One-way fluid communication is established from the central/nurse to the peripheral bioreactors, while fluid isolation is maintained among the peripheral bioreactors by preventing backward fluid flow from the peripheral bioreactors to the central/nurse bioreactor. One of ordinary skill in the art will recognize that any suitable number of peripheral bioreactors may be used, and that this number is not limited to five as illustrated. The illustration of FIG. 1 shows a star configuration in which a central node is formed by the central/nurse bioreactor 102 and the end nodes or points of the star are formed by the peripheral bioreactors 104, 106, 108, 110, 112.

Sterility may be achieved in the bioreactor system using any suitable technique, for example, gamma irradiation or autoclave. In some embodiments, all modules of a distributed system may be sterilized together to simplify start-up, operation and exchanges of modules. Exchanges of modules in the bioreactor system may be performed at any time using sterile connectors.

Coupling additional modular peripheral bioreactors to the central/nurse bioreactor increases the overall size of the cell production system. The modularity of the peripheral bioreactors enables a scale-up free design of an exemplary bioreactor system that avoids the disadvantages of a conventional scale-up technique. For example, the modularity of the peripheral bioreactors facilitates additional modular units to be coupled to the central/nurse bioreactor easily and efficiently, without sterilizing, retesting or reconfiguring the entire system, in order to scale up the overall cell culture volume of the system. This modular way of scaling up the cell culture volume avoids the use of larger bioreactors for scale-up, which is a significant disadvantage of conventional bioreactor systems that use larger and larger bioreactors to increase cell culture capacity and volume. Another significant advantage of the exemplary system is that there is no need for reconfiguring the operation of the system to accommodate the differing conditions and operations in larger bioreactors. The modularity of the peripheral bioreactors enables detection of process deviations and contamination or process end, and easy and efficient segregation or restart of an affected peripheral bioreactor branch without disrupting the entire system.

The distributed system is configured such that one-way fluid communication is established from the central/nurse bioreactor to each of the peripheral bioreactors. That is, fluid is allowed to flow from the central/nurse bioreactor to the peripheral bioreactors in a controlled manner, but fluid is not allowed to flow from the peripheral bioreactors to the central/nurse bioreactor. This particular fluid flow may be achieved in the distributed system using any suitable means including, but not limited to, pumps, valves, manifolds, conduits, and the like. In one embodiment, a multi-way manifold is coupled to an outlet port of the central/nurse bioreactor, and a one-way fluid conduit is used to couple each peripheral bioreactor to the multi-way manifold. The one-way fluid conduit enables fluid flow only from the central/nurse to the peripheral bioreactor, thus maintaining sterility of each bioreactor and preventing contamination or process deviation in one bioreactor from affecting any of the other bioreactors. Although exemplary embodiments are described with reference to a multi-way manifold coupled between a central/nurse bioreactor and a plurality of peripheral bioreactors, one of ordinary skill will understand that any suitable mechanism may be used to provide sequential one-way fluid flow from the central/nurse to the peripheral bioreactors.

Further, providing the peripheral bioreactors in the illustrated configuration enables isolation of a sterile modular peripheral unit that is experiencing contamination or a process deviation or process end. Upon detection of contamination or a process deviation or process end, the affected unit may be cut off automatically (e.g., by shutting off fluid communication from the multi-way manifold to the affected unit), thereby preventing the contamination or process deviation from affecting the other units. Since there is no fluid communication from any peripheral unit to the central/nurse bioreactor, there is no risk of contaminated liquid being transferred back to the central/nurse bioreactor and thereby to the other peripheral units. That is, fluid isolation among the peripheral bioreactors prevents any non-centralized failure from affecting the overall system of bioreactors.

Exemplary embodiments also provide bioreactor control computing devices, computing systems and computer-implemented and computer-executable methods configured or programmed to automatically control the operation of one or more bioreactors (e.g., perfusion bioreactors) based on real-time detection and determination of operating conditions. Exemplary embodiments thereby automate the operation and control of bioreactors so that little or no user intervention is required. Exemplary embodiments thereby allow lab technicians, who are not experts in perfusion, to manage a continuous production of cells, recombinant proteins, monoclonal antibodies, over long periods of time without interruption. In some embodiments, a bioreactor is operated in a completely closed loop, i.e., no samples need to be taken to obtain process information. Human intervention may therefore be limited to connecting or disconnecting fluid conduits to couple the different components of the bioreactor system. The real-time control greatly reduces or eliminates the need for human intervention on the culture, which drastically reduces the risk of contamination.

Exemplary automated control also enables reproducible manufacture of consistent-quality cells at low, medium or high cell concentrations and ensures that the desired bioprocess characteristics (e.g., specific growth rate, growth medium chemical composition, rate of perfusion, maximum cell concentration, and the like) are achieved. The real-time control maintains substantially constant conditions for cells for the duration of the batch, ensuring predictability and reproducibility, batch after batch.

Any suitable biological cell culture may be produced and maintained in an exemplary distributed bioreactor system. Exemplary cells may include, but are not limited to, mammalian cells, insect cells, animal cells, human cells, plant cells, anchorage-dependent cells, transgenic cells, genetically modified cells and other eukaryotic cells, and the like. A cell culture produced and maintained using exemplary bioreactor systems may be used to produce any suitable targeted biological product. In one embodiment, a cell culture may be produced and maintained to produce a targeted recombinant protein. Exemplary targeted recombinant proteins may include, but are not limited to, antibodies, a biologically targeted product thereof, and the like.

In an exemplary distributed bioreactor system (e.g., distributed perfusion bioreactor system), any suitable bioreactor (e.g., perfusion bioreactor) may be used as the central/nurse and peripheral bioreactors including, but not limited to, acoustic, alternating tangential flow (ATF, detailed at http://www.refinetech.com, the contents of which are incorporated herein in their entirety by reference), settler, and the like. In a non-limiting example, a Cell-tainer single-use bioreactor may be used. Details on an exemplary Cell-tainer bioreactor can be found at http://www.celltainer.com. Specific disposable designs may be used to avoid dead volumes in the bioreactors to avoid problems with leaching and extractable issues regardless of the length of the batch. In some examples, disposable, reusable or semi-disposable bioreactors may be used. Any combination of hardware design may be used for the different bioreactors.

In an exemplary distributed bioreactor system, any suitable perfusion device may be used. In one example, a disposable perfusion device may be used, for example the device described in European Patent Application No. 13164759.6, filed Apr. 22, 2013, the entire contents of which are incorporated herein by reference. In some embodiments, disposable conduits, tubing, pumps, bag assemblies and perfusion devices are used instead of hard piping and reusable devices.

An exemplary distributed bioreactor system may include any suitable number of peripheral bioreactors, i.e., bioreactors that are coupled to the nurse/central bioreactor but that are isolated from one another, including, but not limited to, 2, 3, 4, 5, 6, 7, 8, 9, 10, 11, 12, 13, 14, 15, 16, 17, 18, 19, 20, and the like.

It is noted that each peripheral bioreactor (e.g., bioreactor 104, 106, 108, 110 and/or 112) of the system can also be or become a nurse or central bioreactor (e.g., similar to bioreactor 102) for one or more peripheral bioreactors (e.g., each peripheral bioreactor can be or become a nurse/central bioreactor for a new set of additional layer(s) of peripheral bioreactors). For example, in one embodiment, at least one peripheral bioreactor of the system can serve as a nurse or central bioreactor for one or more peripheral bioreactors. Further by way of example, at least two, three, four, five or six peripheral bioreactors of the system can serve as a nurse or central bioreactor for one or more peripheral bioreactors.

It is also noted that out of the additional layer(s) of peripheral bioreactors, one or more of these additional bioreactors can also be or become a nurse or central bioreactor (e.g., similar to bioreactor 102) for one or more peripheral bioreactors (e.g., each additional peripheral bioreactor in each added layer of bioreactors can be or become a nurse/central bioreactor for a new set of additional layer(s) of peripheral bioreactors).

In some embodiments, each peripheral bioreactor may have substantially the same footprint, the same design and/or substantially equal minimum and maximum working volumes. This enables easy addition of peripheral bioreactors to achieve consistent performance without redesigning, reconfiguring or retesting the system. In other embodiments, the peripheral bioreactors may have different designs and/or different working volumes.

Exemplary bioreactors may have any suitable volume including, but not limited to, about 1 L to about 500 L, but are not limited to this exemplary range. Certain exemplary bioreactor volumes include, but are not limited to, about 1, 2, 3, 4, 5, 6, 7, 8, 9, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300 L, any intermediate volumes, and the like. An exemplary bioreactor vessel may have any suitable minimum and maximum working volumes depending, for example, on the total vessel volume, the ratio between the height and diameter of the vessel, the vessel configuration (e.g., whether the bioreactor is a bag bioreactor), the growth rate, and the like. For example, in a 5 L bioreactor, an exemplary minimum working volume may range from about 100 mL to about 1 L, and an exemplary maximum working volume may range from about 3.5 L to about 5 L. In a 20 L bioreactor, an exemplary minimum working volume may range from about 100 mL to about 5 L, and an exemplary maximum working volume may range from about 15 L to about 19 L. In a 200 L bioreactor, an exemplary minimum working volume may range from about 20 mL to about 50 L, and an exemplary maximum working volume may range from about 150 L to about 190 L. One of ordinary skill in the art will recognize that the above numerical values and ranges are illustrative and not intended to limit the scope of the invention.

Exemplary peripheral bioreactors may have working volumes ranging from about 20 liters to about 200 liters, but are not limited to this exemplary range. An exemplary nurse/central bioreactor may have working volumes ranging from about 5 liters to about 20 liters, but is not limited to this exemplary range.

Exemplary distributed bioreactor systems may be configured to maintain the cell culture continuously for extended periods of time, including, but not limited to, more than a month, more than two months, more than three months, more than six months, and the like. In some embodiments, the cell culture may be maintained continuously for a number of days, including, but not limited to, 1, 5, 10, 15, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300 days, any intermediate numbers, and the like.

Figure 2:
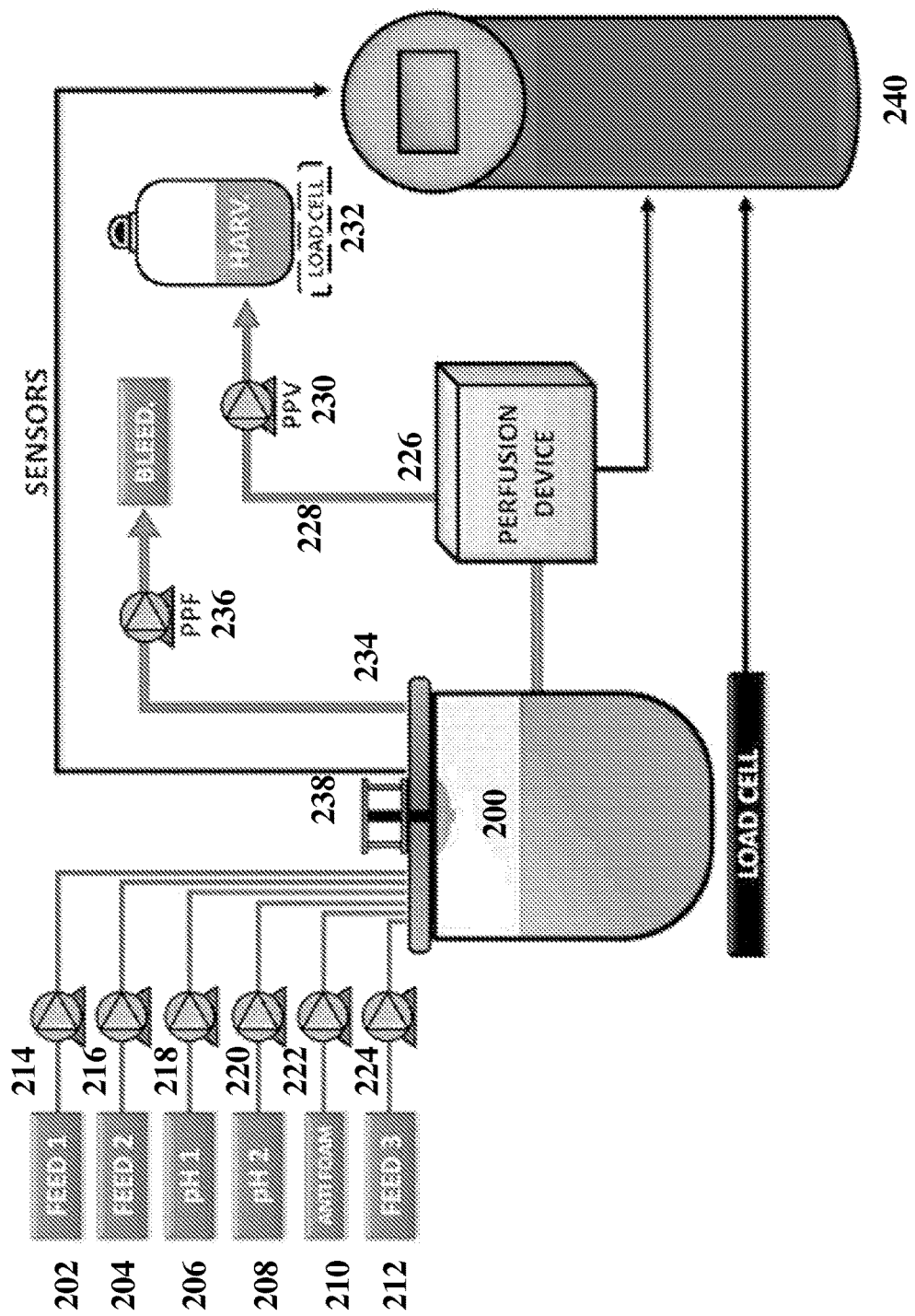
FIG. 2 is a schematic illustrating an exemplary perfusion bioreactor (central or peripheral) coupled to a perfusion device and a control device.
Figure 3:
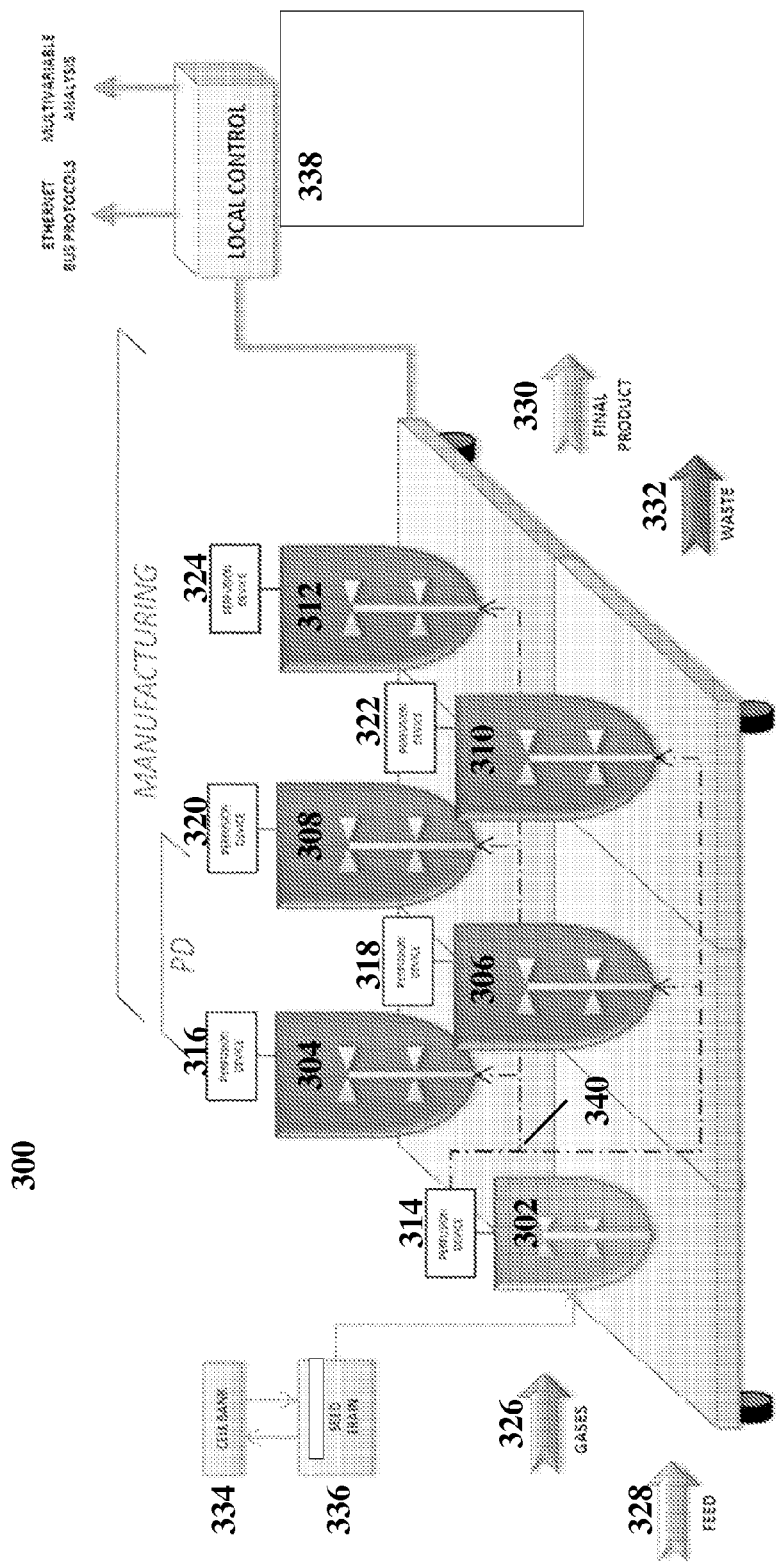
FIG. 3 is a schematic illustrating a distributed perfusion bioreactor system including a central bioreactor and a plurality of peripheral bioreactors.
Figure 4:
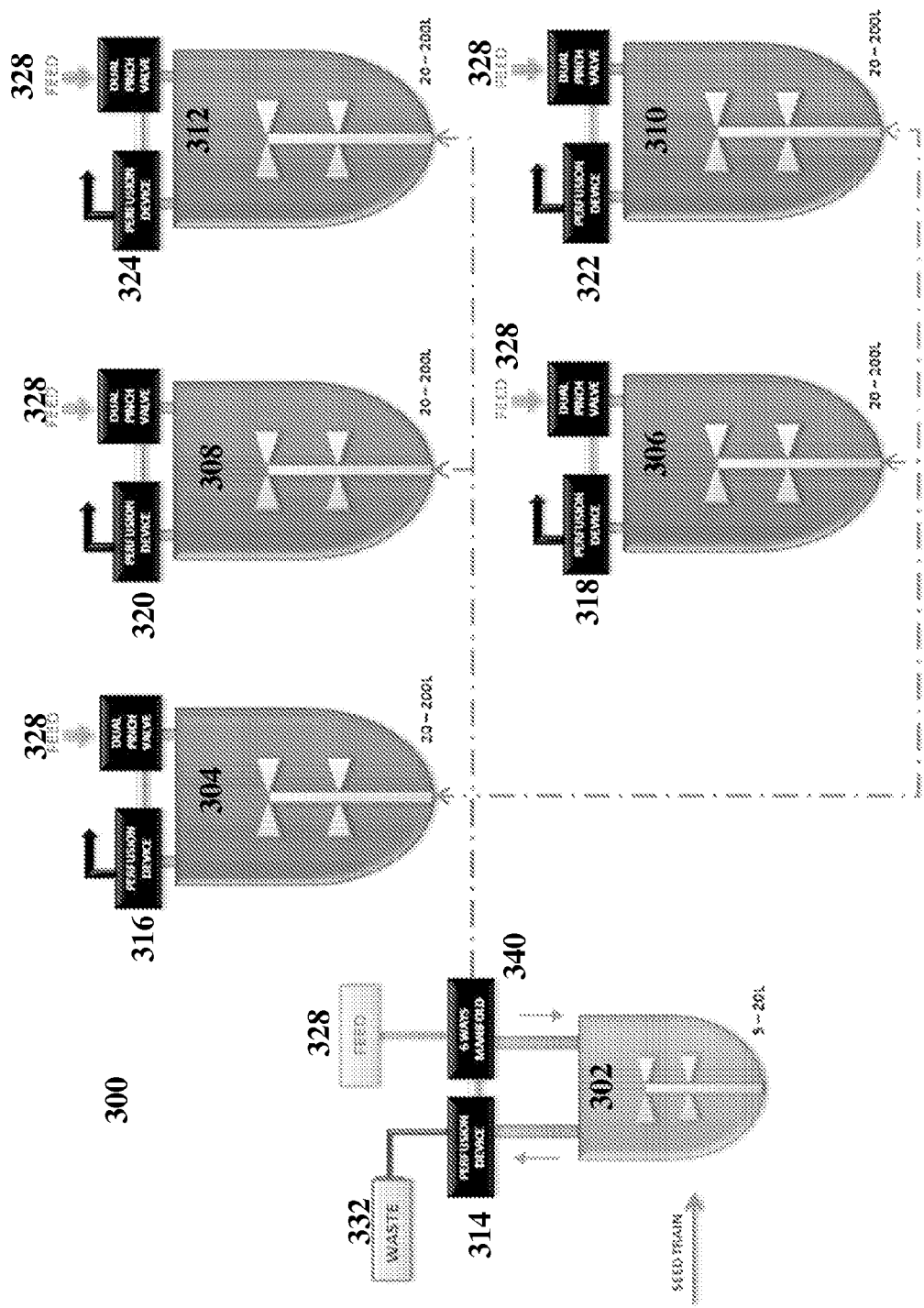
FIG. 4 is a schematic illustrating a distributed perfusion bioreactor system including a central bioreactor and a plurality of peripheral bioreactors.

An exemplary bioreactor 200 is described in more detail with reference to FIG. 2. The bioreactor 200 may be a disposable bioreactor in one embodiment. The bioreactor 200 may include one or more inlet ports 202, 204, 206, 208, 210, 212 for introduction of one or more feeds (e.g., cell culture medium), chemical substances (e.g., pH buffers), anti-foam agents, and the like. Each inlet and outlet port in the bioreactor 200 may be provided with any suitable mechanism for initiating and conducting fluid flow through the port including, but not limited to, one or more peristaltic pumps, one or more pressurization mechanisms, and the like. Each medium inlet port may be provided with any suitable mechanism for monitoring and controlling fluid flow through the port including, but not limited to, one or more mass flow meters, one or more flow control valves, and the like. For example, the bioreactor 200 may include a flow control mechanism 214, 216, 218, 220, 222, 224 to control the flow rate of substances into the bioreactor 200.

The bioreactor 200 may be coupled to a perfusion device 226 that may be operated at discrete times or continuously to perfuse the cell culture with cell culture medium. The bioreactor 200 may include one or more outlet ports for releasing spent cell culture, cells and/or biological products. A harvest outlet port 228 may be provided at the perfusion device 226 or the bioreactor 200 itself for harvesting spent medium (which may contain biological of interest) from the bioreactor 200 while keeping cells within the bioreactor. A flow control valve 230 may be provided at the harvest outlet port 228 to control the rate of harvest. In one embodiment, the harvested product may be stored in a harvest bottle or container 232. A bleeding port 234 may be provided at the bioreactor 200 to allow release or bleeding of cells from the bioreactor 200. A flow control valve 236 may be provided at the bleeding port 234 to control the bleed rate.

The bioreactor 200 may include one or more sensors or probes 238 for detecting one or more operational parameters in real-time including, but not limited to, a state of inlet ports, a state of outlet ports, a state of a multi-way manifold, a capacitance probe, a cell culture volume sensor, a cell culture weight sensor, a liquid level sensor, a thermometer, a pH probe, an oxygen probe, a lactic acid probe, an ammonia probe, a rate of agitation sensor, a metabolic flux sensor, a metabolic rate sensor, a perfusion rate sensor, a carbon monoxide sensor, mass spectrometry, gas chromatography, combinations thereof, and the like. These sensors 238 may detect one or more operational parameters including, but not limited to, a viable cell density (using the capacitance probe or any alternative method providing online measurements of cell density), a cell culture volume, a cell culture weight, a cell culture liquid level, a temperature, a pH, dissolved oxygen, agitation rate, metabolic flux, metabolic rate, a perfusion rate of a perfusion device, oxygen uptake rate, carbon dioxide production (e.g., using gas chromatography, mass spectrometry), lactic acid levels, ammonia levels, combinations thereof, and the like.

The bioreactor 200 (and its inlet ports, outlet ports, perfusion device, and the like) may be coupled to a control device 240 configured or programmed to perform multivariate analysis of sensor data and to automatically control operation of the bioreactor in real-time based on the analysis. The control device 240 may control operation by, for example, opening/closing a port, turning on/off the perfusion device, changing the state of the multi-way manifold, changing a rate of perfusion of the perfusion device, changing a rate of agitation of the cell culture, a temperature, a pH, a level of dissolved oxygen, combinations thereof, and the like.

In some embodiments, an exemplary bioreactor system may use anionic exchange membrane technology, such as reverse electro-enhanced dialysis (REED) technology designed by JURAG (www.jurag.dk). When integrated to fermentation or cell culture processes, Jurag's REED technology can separate small molecular compounds from a broth helping to control and improve the cell growth processes and to reduce the quantity of cell growth media consumed by the increasing cell population. In some cases, a perfusion rate and feeding of medium may be controlled based on data received from anionic exchange membrane technology, such as REED.

An exemplary distributed bioreactor system 300 is described in more detail with reference to FIGS. 3-6. During a manufacturing stage, a central/nurse bioreactor 302 and a plurality of peripheral bioreactors 304, 306, 308, 310, 312 may be used. In some embodiments, each peripheral bioreactor and its corresponding fluid conduits (e.g., a one-way fluid conduit for coupling to the central/nurse bioreactor) may be pre-assembled to form a sterile modular unit suitable for coupling to the central/nurse bioreactor via the multi-way manifold to scale up a volume of the cell culture of the distributed bioreactor system (e.g., distributed perfusion bioreactor system). During a process development (PD) stage, a smaller subset of peripheral bioreactors (e.g., one peripheral bioreactor 304) may be used. The modularity of the peripheral bioreactors enables easy and efficient addition of peripheral bioreactors to scale-up production from the PD stage to the manufacturing stage. The hardware and control device components are the same or similar for the PD and manufacturing stages to avoid the necessity of multiple engineering designs and to reduce delays in the manufacturing and clinical phases.

Each bioreactor is coupled to a corresponding perfusion device 314, 316, 318, 320, 322, 324. Each bioreactor has inlet ports coupled to conduits for introduction of gases 326 and feed or medium 328, and has outlet ports coupled to conduits for release of the targeted biological product 330 and waste/spent feed or medium 332. One-way fluid communication is established from the central/nurse bioreactor 302 to the peripheral bioreactors 304, 306, 308, 310, 312 using a multi-way manifold 340, but fluid isolation is maintained among the peripheral bioreactors 304, 306, 308, 310, 312. The manifold 340 is switchable among the plurality of one-way fluid conduits and is controllable by a control device configured to activate the manifold 340 to sequentially feed cells in the central/nurse bioreactor to at least two of the peripheral bioreactors. The manifold is designed to have redundancy to allow switching from feeding one bioreactor to another bioreactor without interrupting the cell culture process.

In one embodiment, the control device may automatically shut or close off fluid communication between the manifold 340 and a first peripheral bioreactor upon detecting a process deviation or contamination in the first peripheral bioreactor. A contamination may be the presence of one or more undesired substances in the bioreactor system. A process deviation may be one or more undesired physical, environmental or chemical conditions in the bioreactor system. Any suitable mechanism may be used to detect a contamination or a process deviation. In an exemplary embodiment, a cell concentration signal corresponding to the cell density in a bioreactor may be used to detect early-stage process deviations. A control device coupled to the bioreactor system may analyze the cell concentration signal to determine the size distribution of the cells. An anomalous size distribution (e.g., indicating that the average cell radius is 20% larger than a normal cell radius) may be used to determine that a contamination or a process deviation is present. Exemplary embodiments thereby provide an automatic process of detecting contamination and process deviations and the automatic switching of the manifold 340 in response, which is advantageous in avoiding reductions in productivity and other potential issues that are typically caused by contamination and process deviations.

A cell bank 334 is provided for holding a collection of cells and maintaining quality and quantity of the cells at required levels to obtain consistent batches of cell cultures at substantially the same manufacturing conditions. The cell bank 334 may be disposable in one embodiment. The cell bank 334 is coupled to a front-end perfused bioreactor 336 for growing a preliminary cell culture by inoculation using the cell bank 334. The front-end bioreactor 336 is configured to produce and maintain a preliminary cell culture upon inoculation by the cell bank 334. The front-end bioreactor 336 is coupled to the central/nurse bioreactor 302 for one-way transfer of at least part of the cell culture from the front-end bioreactor to the central/nurse bioreactor. The front-end bioreactor 336 may be a disposable bioreactor in one embodiment. The front-end bioreactor 336 may be a bag device or a single-use bioreactor.

Each bioreactor is coupled to one or more control devices 338 that are configured to perform multivariate analysis, automatically control operation of the bioreactors in real-time and, optionally, communicate with bioreactor components remotely (using, for example, network protocols) in order to control bioreactor operation.

Figure 5:
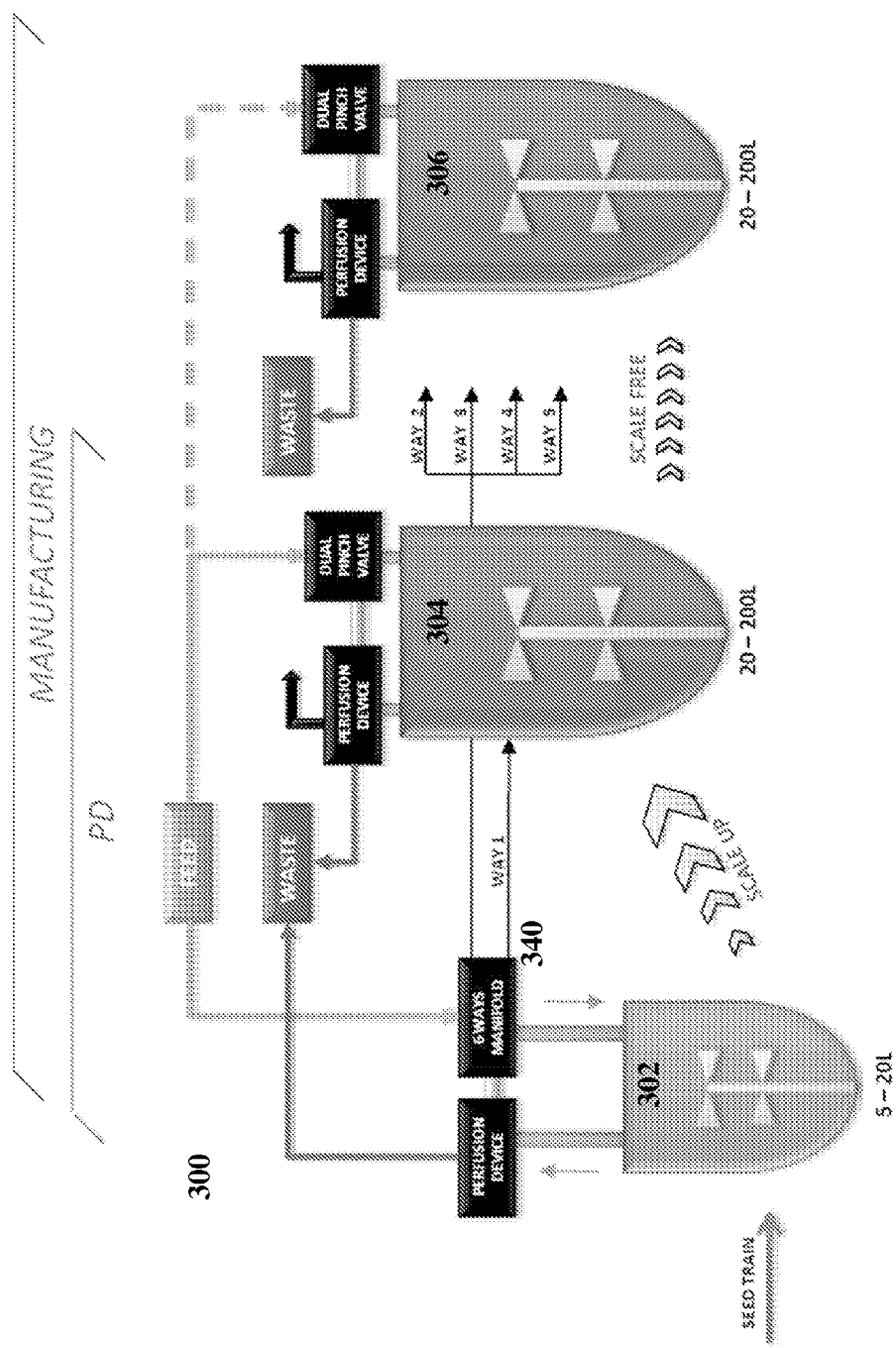
FIG. 5 is a schematic illustrating a distributed perfusion bioreactor system including a central bioreactor and a plurality of peripheral bioreactors.

As illustrated in FIG. 5, an exemplary central/nurse bioreactor 302 may have a working volume ranging from about 5 liters to about 20 liters, and each exemplary peripheral bioreactor 304, 306, 308, 310, 312 may have a working volume ranging from about 20 liters to about 200 liters. One of ordinary skill in the art will recognize that the above working volumes are exemplary and that other working volumes may also be used. Thus, in some embodiments, there is a scale-up of working volume from the central/nurse bioreactor to the peripheral bioreactors. However, the addition of additional peripheral bioreactors is a scale-up free process in that the bioreactors of the same volume may be added to the system in a modular manner. The multi-way manifold 340 enables easy and efficient connection of the modular peripheral bioreactors to the central/nurse bioreactor, without needing to redesign, reconfiguring or retest the entire system.

Figure 6:
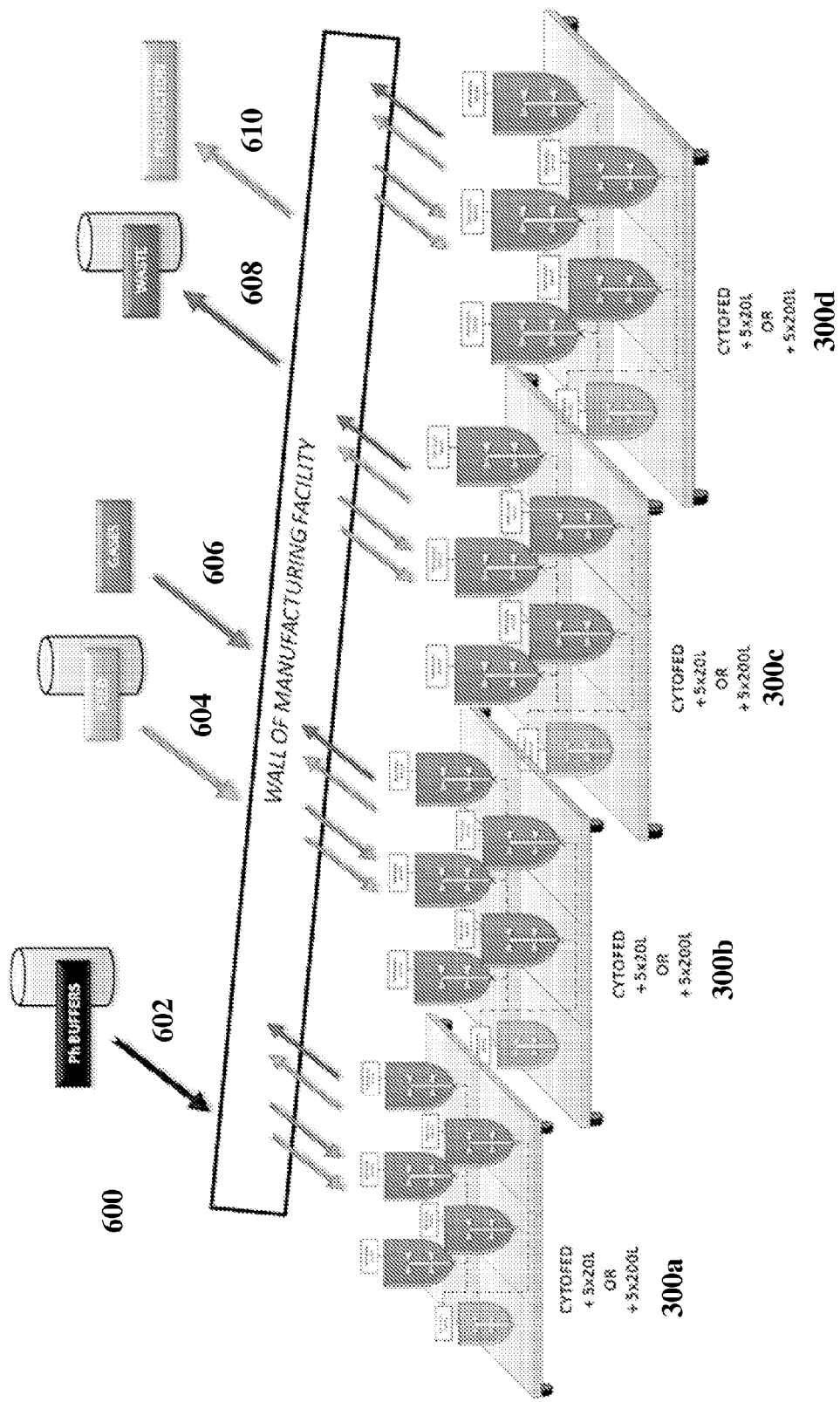
FIG. 6 is a schematic illustrating a large-scale manufacturing platform including multiple distributed perfusion bioreactor systems, each including a central bioreactor coupled to a plurality of peripheral bioreactors.

FIG. 6 is a schematic illustrating a large-scale manufacturing platform 600 using multiple distributed systems 300a-d, each including a central/nurse bioreactor coupled to a plurality of peripheral bioreactors. In some embodiments, a centralized inlet conduit (e.g., for a pH buffer 602, a medium or feed 604, a gas 606) may be provided to introduce a substance into the bioreactors of the entire platform. Such a centralized inlet conduit may branch into multiple inlet conduits in order to couple to the different distributed systems on the platform. In some embodiments, a centralized outlet conduit (e.g., for a waste or spent medium or feed 608, a biological product 610) may be provided to release a substance from the bioreactors of the entire platform. Such a centralized outlet conduit may branch into multiple outlet conduits in order to couple to the different distributed systems on the platform.

Figure 7:
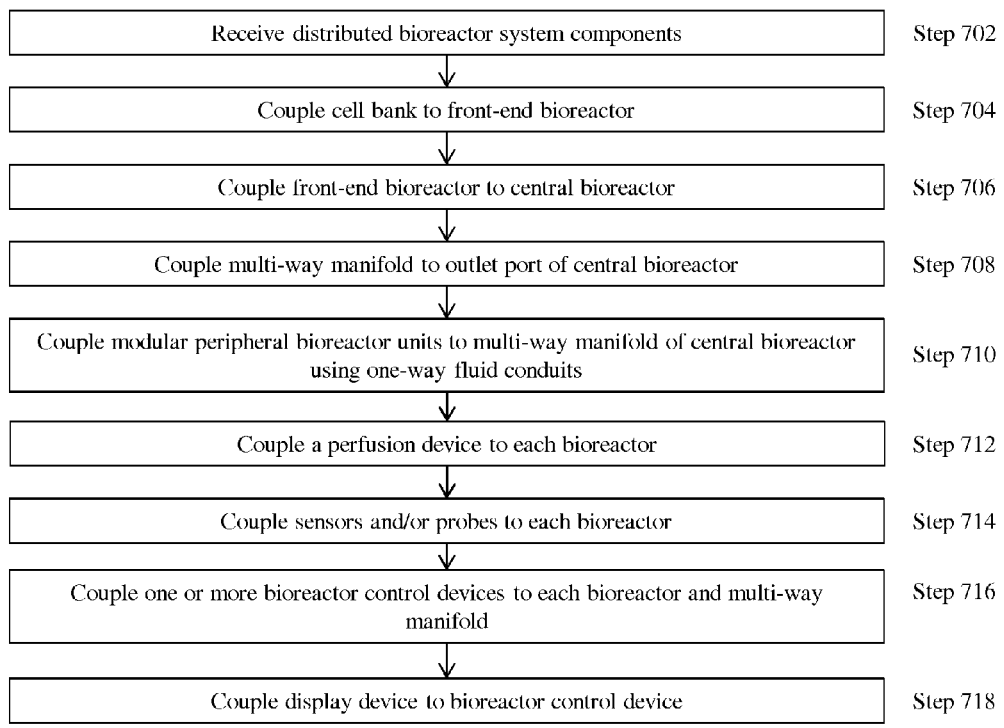
FIG. 7 is a flowchart illustrating an exemplary method for assembling an exemplary distributed perfusion bioreactor system.

FIG. 7 is a flowchart illustrating an exemplary method for assembling any of the distributed bioreactor systems (e.g., distributed perfusion bioreactor systems) shown in FIGS. 3-6. In step 702, at least the following distributed bioreactor system components are received: a cell bank, a front-end perfused bioreactor, a central or nurse perfused bioreactor, a plurality of sterile modular peripheral bioreactor units (each including a peripheral bioreactor), a plurality of perfusion devices, a multi-way manifold, and a plurality of one-way fluid conduits. In one embodiment, these components may be sterile. In step 704, the cell bank is coupled to the front-end bioreactor to enable transfer of cells from the cell bank to the front-end bioreactor. In step 706, the front-end bioreactor is coupled to the central/nurse bioreactor to enable transfer of cells from the front-end bioreactor to the central/nurse bioreactor. In step 708, the multi-way manifold is coupled to an outlet port of the central/nurse bioreactor.

In step 710, each modular peripheral bioreactor unit is coupled to the multi-way manifold using a corresponding one-way fluid conduit, such that one-way fluid communication is established from the central/nurse bioreactor to the peripheral bioreactors and such that fluid isolation is maintained among the peripheral bioreactors. That is, a cell culture may be transferred from the central/nurse to the peripheral bioreactors, but no fluid is transferred between any of the peripheral bioreactors, thus maintaining sterility of each bioreactor and preventing contamination or process deviation in one bioreactor from affecting any of the other bioreactors. Further, providing the peripheral bioreactors in the illustrated configuration enables isolation of a modular peripheral unit that is experiencing contamination or a process deviation. Upon detection of contamination or a process deviation, the affected unit may be cut off automatically (e.g., by shutting off fluid communication from the multi-way manifold to the affected unit), thereby preventing the contamination or process deviation from affecting the other units. Since there is no fluid communication from any peripheral unit to the central/nurse bioreactor, there is no risk of contaminated liquid being transferred back to the central/nurse bioreactor and thereby to the other peripheral units. That is, fluid isolation among the peripheral bioreactors prevents any non-centralized failure from affecting the overall system of bioreactors.

In step 712, a perfusion device can be coupled to each or some of the bioreactors in the system in order to enable retention of cells during their operation. In step 714, one or more probes or sensors are coupled to each bioreactor. In step 716, one or more control device are coupled to each bioreactor and the multi-way manifold for independently controlling the operation of each bioreactor in real-time. In one embodiment, a separate control device may be assigned to control the operation of a single bioreactor. In another embodiment, the same control device may be assigned to control the operation of multiple or all of the bioreactors. The control devices may be configured to receive data from the sensors coupled to the bioreactors and may be configured to control the operation of the bioreactors automatically based on the received data and/or based on analysis and determinations based on the received data.

In step 718, a display device may be coupled to the control devices for rendering an intuitive and easy-to-use user interface between the bioreactor system and a user of the system. The user interface may display or otherwise provide information regarding the bioreactor system and its components to the user, and/or may receive input from the user regarding control of the bioreactor system. A user may need to be trained to use the interface a single time and would not require extensive and expert training in the operation of bioreactors in order to monitor the system.

Once a distributed bioreactor system is assembled, the system may be operated to produce and maintain a continuous biological cell culture.

III. Exemplary Automated Bioreactor Operation

Exemplary embodiments provide computing devices, computing systems and computer-implemented and computer-executable methods configured or programmed to automatically control the operation of one or more bioreactors based on real-time detection and determination of operating conditions. In some embodiments, exemplary devices, systems and methods of automatic control may be implemented to control the bioreactors in a distributed bioreactor system, for example, the exemplary system illustrated in FIGS. 3-6. In some embodiments, exemplary devices, systems and methods of automatic control may be implemented independently in any bioreactor that may or may not be part of a distributed system.

Many cell culture processes are based on perfusion or fed-batch bioreactor systems. Conventional control for introducing medium and for maintaining steady-state conditions in bioreactors requires substantial intervention from trained users and can be especially challenging due to high and fluctuating cell concentrations that can rapidly change environmental conditions in a bioreactor. Conventional control of perfused bioreactors, based on infrequent daily sampling and estimation of the live cell concentration, can therefore lead to large process deviations. In contrast, in exemplary embodiments, tight control of the perfusion or concentrate addition rate using real-time online cell concentration measurements allows bioreactors to be operated under optimum conditions for maximum recombinant protein production.

In order to avoid the technical challenges inherent in conventional bioreactor operation, exemplary embodiments automate the operation and control of a bioreactor to require no or minimal user intervention. Exemplary embodiments thereby allow lab technicians, who are not experts in perfusion, to manage a continuous production of cells, recombinant proteins, monoclonal antibodies, over long periods of time without interruption. In some embodiments, a bioreactor is operated in a completely closed loop, i.e., no samples need to be taken to obtain process information. Human intervention may be limited to connecting or disconnecting fluid conduits to couple the different components of the bioreactor system. The real-time control greatly reduces or eliminates the need for human intervention on the culture, which drastically reduces the risk of contamination.

Exemplary automated control also enables reproducible manufacture of consistent-quality cells at low, medium or high cell concentrations and ensures that the desired bioprocess characteristics (e.g., specific growth rate, growth medium chemical composition, rate of perfusion, maximum cell concentration, and the like) are achieved. The real-time control maintains substantially constant conditions for cells for the duration of the batch, ensuring predictability and reproducibility, batch after batch.

Automated control is achieved in exemplary embodiments using a bioreactor control computing device implementing one or more control devices. The control devices may receive data from one or more sensors or probes in the bioreactor. An exemplary control device may control operation of a bioreactor by, for example, opening/closing a port, turning on/off the perfusion device, changing a state of the multi-way manifold, changing a rate of perfusion of the perfusion device, changing a rate of agitation of the cell culture, a temperature, a pH, a level of dissolved oxygen, combinations thereof, and the like. In some embodiments, a robust automatic perfusion rate control system may be operated based on one or more conditions in the bioreactor, for example, data sensed in real-time from capacitance probes (e.g., online radio-frequency impedance probes or any other suitable technique of measuring cell density online) used during perfusion. The data from the cell concentration probes may be used to determine a measure of viable cell density of the cell culture which, in turn, may be used to control one or more operational parameters in real-time. These operational parameters may include, but are not limited to, a perfusion rate of a perfusion device, open or closed state of a medium inlet port, open or closed state of a medium outlet port, a medium inlet rate, a medium outlet rate, combinations thereof, and the like. In some embodiments, one or more other bioreactor factors (e.g., pH, dissolved oxygen, and the like) may be monitored in real-time and may be used to control operational parameters.

In operation of a distributed bioreactor system, a central/nurse bioreactor is provided or inoculated with a biological cell culture. The central/nurse bioreactor is operated to grow and maintain the cell culture in one or more sequential operational states including, but not limited to, one or more of: batch, fed-batch, perfused batch, perfused fed-batch, and cytostat states. Portions of the cell culture may be transferred from the cell culture to one or more of the peripheral bioreactors at one time, at multiple time points or continually based on the requirements of the peripheral bioreactors. The transfer of the culture to each bioreactor may be controlled quantitatively or qualitatively using, for example, data from a cell concentration probe, analytical methods, and the like. The peripheral bioreactors may each be operated to grow and maintain the cell culture in one or more sequential operational states including, but not limited to, one or more of: batch, fed-batch, perfused batch, perfused fed-batch, and cytostat states. The bioreactors may be in a stand-by mode when not operational.

Figure 8:
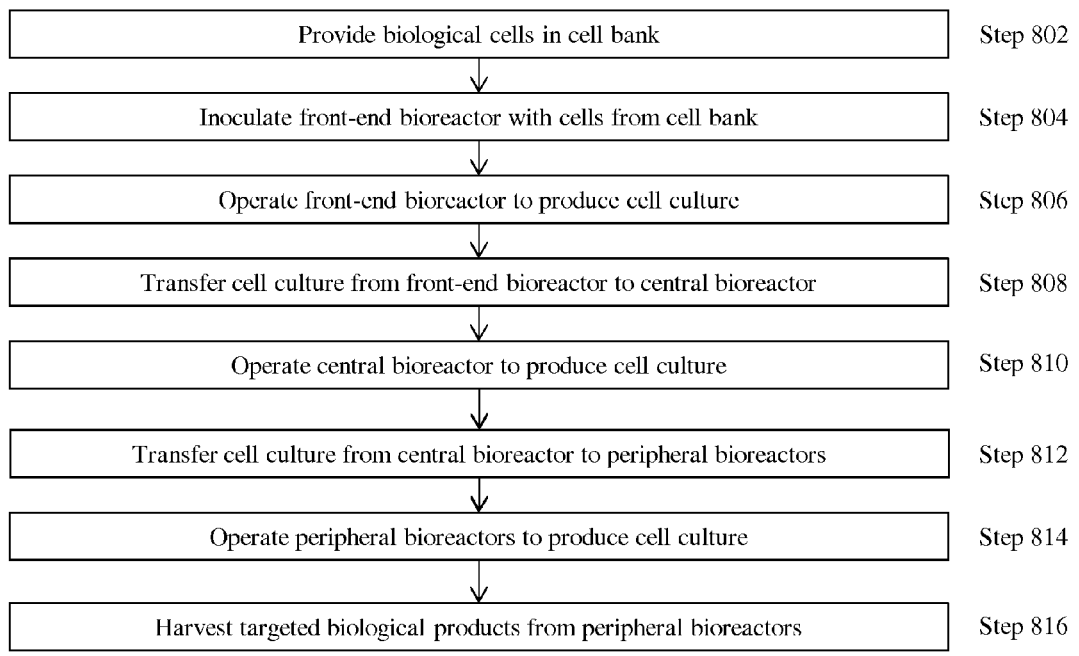
FIG. 8 is a flowchart illustrating an exemplary method for operating an exemplary distributed perfusion bioreactor system.

FIG. 8 is a flowchart illustrating an exemplary method for operating a distributed bioreactor system, e.g., as shown in FIGS. 3-6. In step 802, biological cells are provided in the cell bank or the cell bank already contains cells. In step 804, the front-end bioreactor is inoculated with cells from the cell bank. In step 806, the front-end bioreactor is operated to produce and maintain a continuous cell culture. In step 808, a portion of the cell culture is transferred from the front-end bioreactor to the central/nurse bioreactor. In step 810, the central/nurse bioreactor is operated produce and maintain a continuous cell culture. In step 812, when a desired cell concentration and/or cell culture volume is reached in the central/nurse bioreactor, a portion of the cell culture is transferred via the multi-way manifold to one or more of the peripheral bioreactors. The cell culture may be transferred sequentially to a plurality of peripheral bioreactors or may be transferred at the same time. In step 810, the peripheral bioreactors are each operated produce and maintain a continuous cell culture. In step 816, one or more products of the cell culture may be harvested from the peripheral bioreactors at a single time or at multiple times.

Although the steps of FIG. 8 are illustrated in the form of a flowchart, one of ordinary skill in the art will recognize that one or more of the steps may be performed concurrently, for example, steps 806, 810 and 814.

Within steps 806 and 810 of FIG. 8, a central/nurse or peripheral bioreactor is typically operated in a series of operational states. Exemplary operational states include, but are not limited to, batch, fed-batch, perfused batch, perfused fed-batch and cytostat.

Prior to operation, the steps and the sequencing of steps in the operation of the bioreactors in step 806 and/or step 810 in FIG. 8 may be configured automatically by a control device based on the cell culture being produced or a desired biological product of the cell culture. For example, based on the cell culture or desired product, a particular series of one or more operational states may be chosen and automatically set for a bioreactor. This avoids the need for manual configuration of the bioreactors based on the desired product. The automatic configuration of the bioreactors enables fast and efficient setup of the system and production with minimal user involvement.

During operation, the control device may control, in real-time, operational parameters to establish the conditions necessary for each stage of the bioreactor's operation. For example, the medium inlet port, medium outlet port, perfusion rate of the perfusion device, gas inlet, bleed outlet port, and the like, may be controlled in real-time based on a particular bioreactor's operational parameters (e.g., which operational state it is in, its cell concentration, its cell culture volume, and the like). Further, a control device may be used to automatically transition a given bioreactor from a first operational state to a second operational state based on data on the operating conditions of the bioreactor (e.g., culture volume and/or viable cell density).

Figures 9A, 9B:
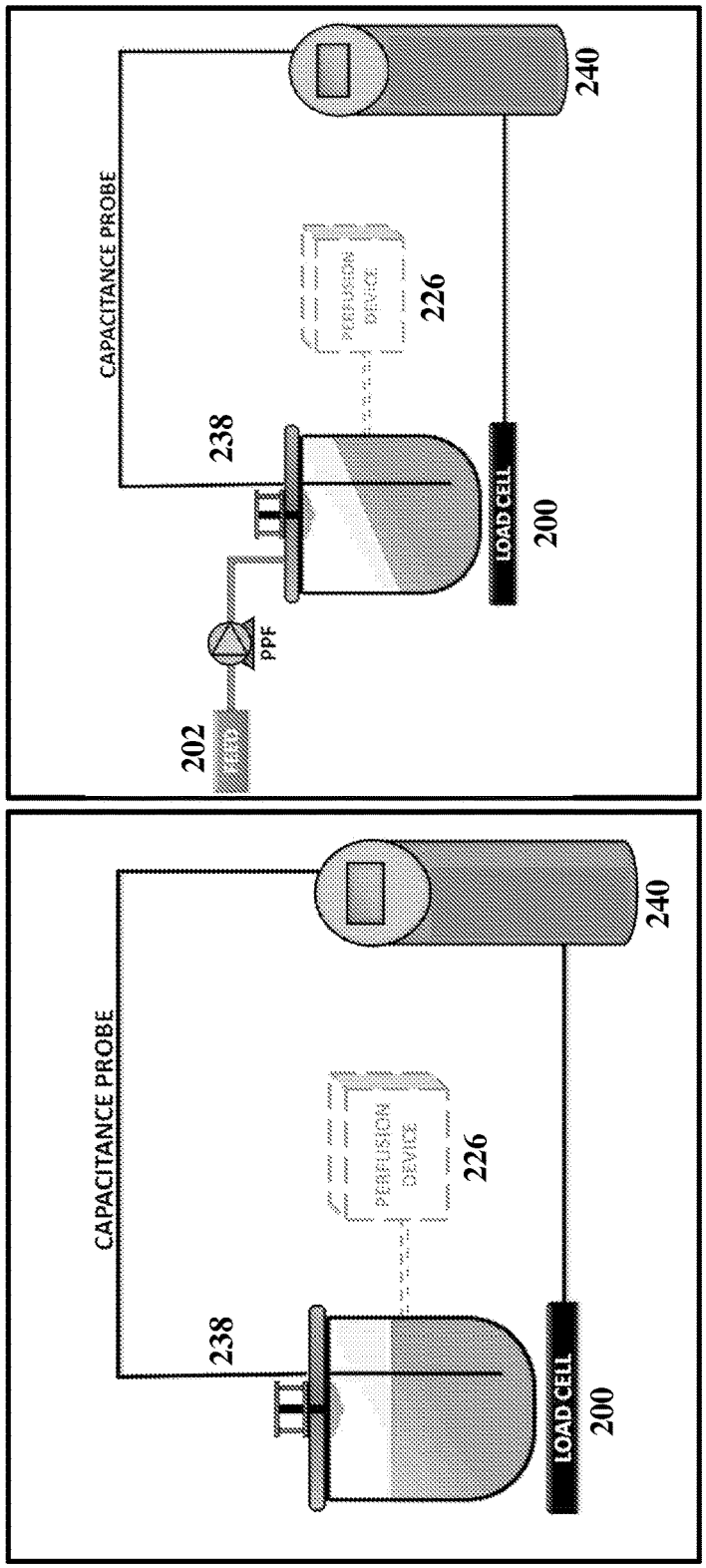
FIG. 9A is a schematic illustrating a batch operational state in a bioreactor.
FIG. 9B is a schematic illustrating a fed-batch operational state in a bioreactor.
Figure 9C:
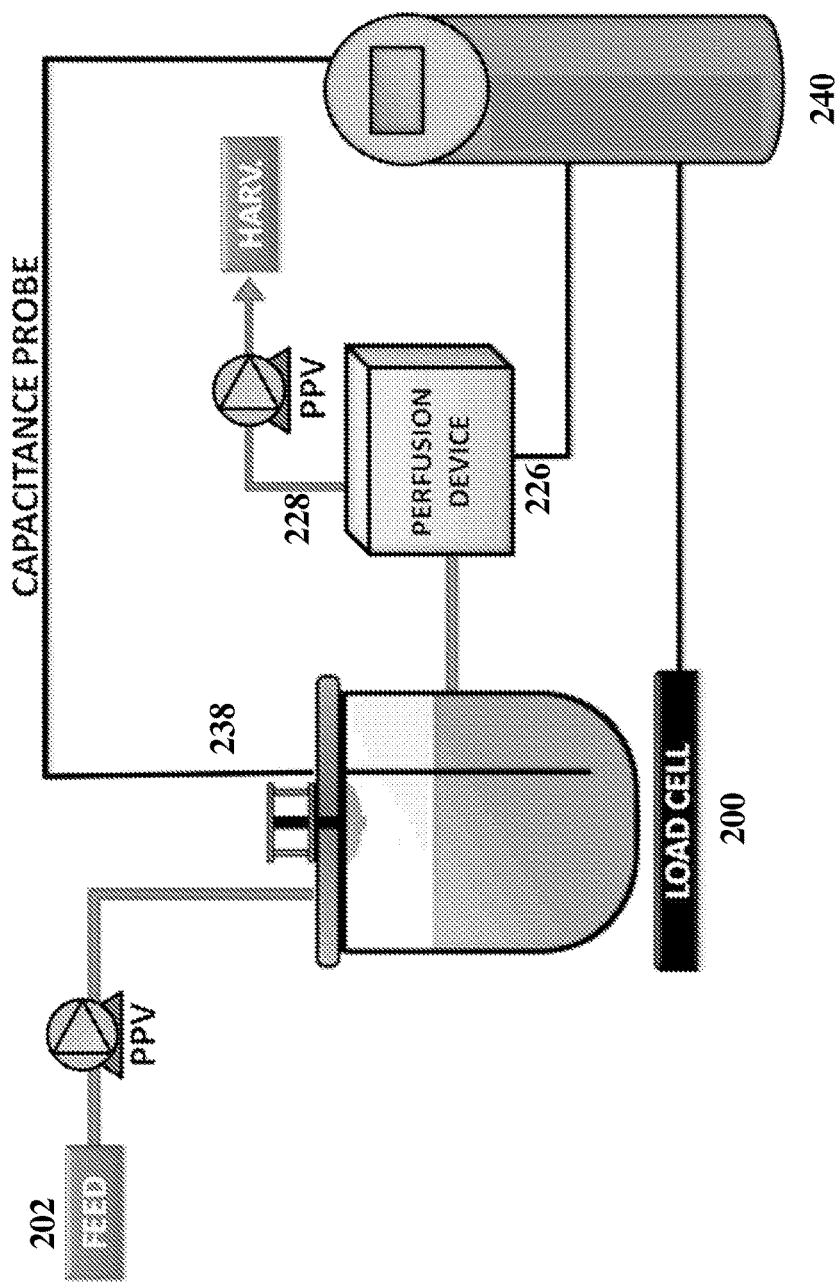
FIG. 9C is a schematic illustrating a perfused batch operational state in a bioreactor.
Figure 9D:
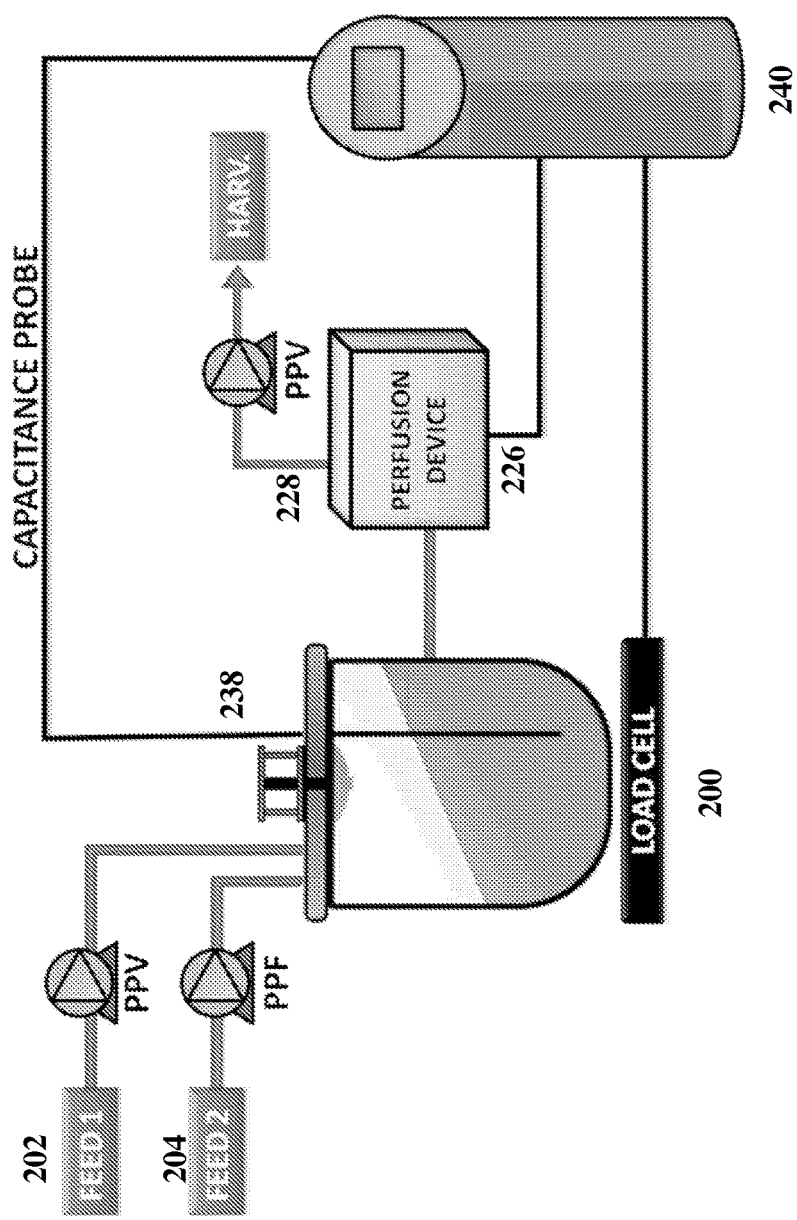
FIG. 9D is a schematic illustrating a perfused fed-batch operational state in a bioreactor.
Figure 9E:
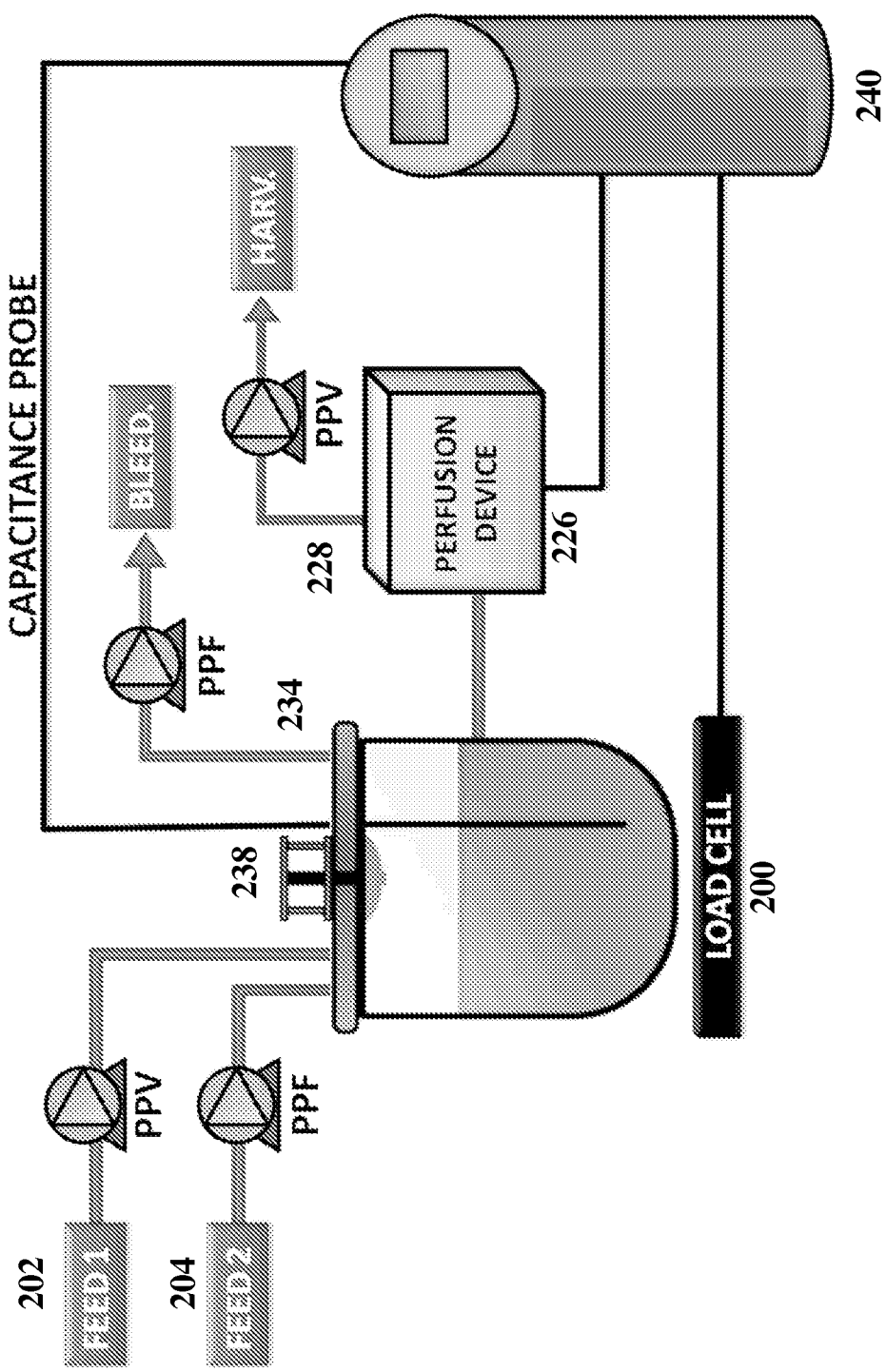
FIG. 9E is a schematic illustrating a perfusion operational state in a bioreactor.
Figure 10A:
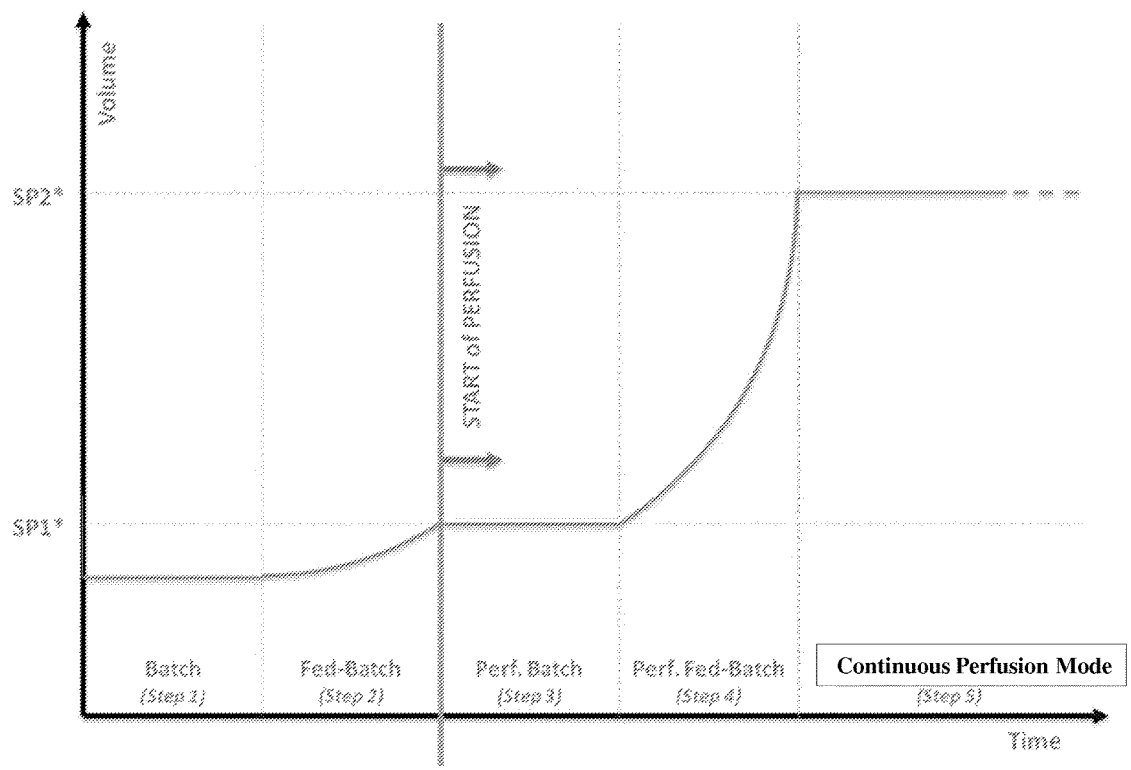
FIG. 10A is a graph of cell culture volume in a bioreactor during batch, fed-batch, perfused batch, perfused fed-batch and perfusion operational states, indicating exemplary predefined cell culture volume thresholds (SP1* and SP2*).
Figure 10B:
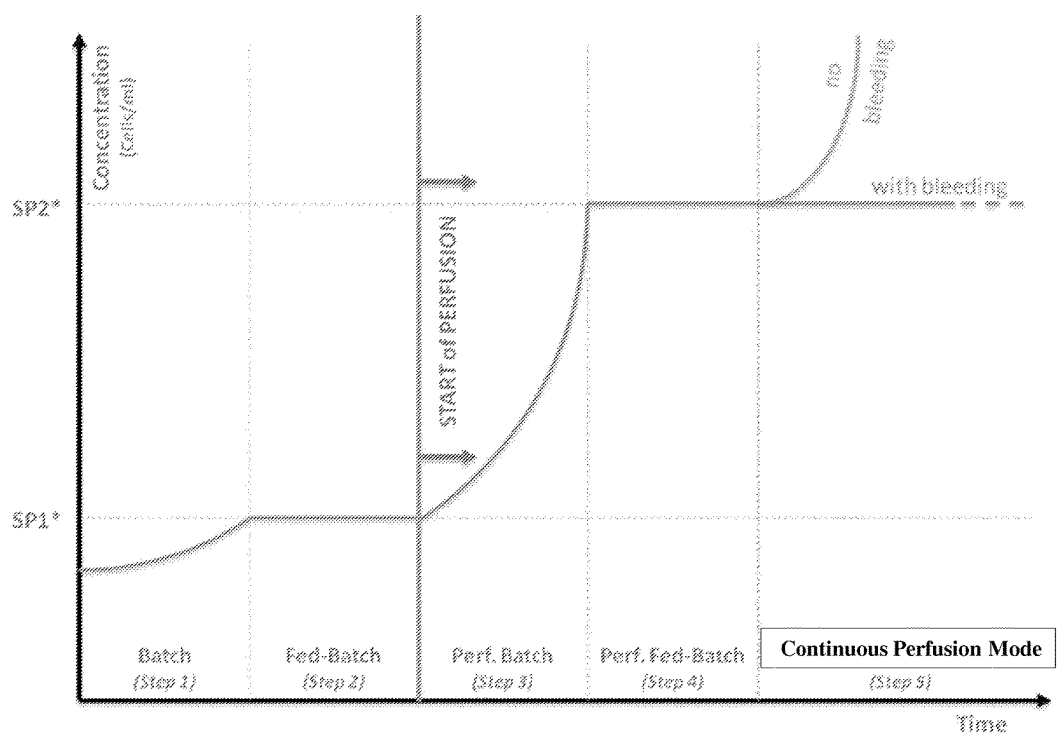
FIG. 10B is a graph of cell concentration in a bioreactor during batch, fed-batch, perfused batch, perfused fed-batch and perfusion operational states, indicating exemplary predefined cell concentration thresholds (SP1* and SP2*).

Details on each operational state of a bioreactor are described with respect to FIGS. 9A-9E and FIGS. 10A-10B. FIGS. 9A-9E are schematics illustrating exemplary operation of a bioreactor 200 coupled to a perfusion device 226 and a control device 240 (also illustrated in FIG. 2) in the following operational states, respectively: batch, fed-batch, perfused batch, perfused fed-batch and cytostat. FIG. 10A is a graph of the volume of the cell culture in the following operational states: batch, fed-batch, perfused batch, perfused fed-batch and cytostat. FIG. 10B is a graph of the cell concentration of the cell culture in the following operational states: batch, fed-batch, perfused batch, perfused fed-batch and cytostat.

FIG. 9A illustrates a batch state of operation in which the perfusion device 226 is turned off, medium inlet ports 202, 204, 212 of the bioreactor 200 are shut or closed off (so that cell growth medium is not introduced into the bioreactor), and medium outlet ports 228, 234 of the bioreactor are shut or closed off (so that spent medium or cells are not released from the bioreactor). During the batch state, the cell concentration of the cell culture in the bioreactor grows while the volume of the cell culture is kept substantially constant. This is illustrated as Step 1 in FIGS. 10A and 10B.

FIG. 9B illustrates a fed-batch state of operation in which the perfusion device 226 is turned off, one or more medium inlet ports 202, 204, 212 of the bioreactor 200 are opened (so that cell growth medium is introduced into the bioreactor), and the introduction of the medium is controlled by a control device 240, in real-time, to maintain the cell concentration at a substantially constant level. A cell concentration probe or sensor 238 may be used to detect the viable cell density in real-time in order to determine, in real-time, the fluid flow that is needed to maintain the cell concentration at a substantially constant level. Any suitable mechanism may be used to control the medium flow including, but not limited to, a flow control mechanism 214, 216, 224. In some embodiments, a growth limiting nutrient may be introduced into the bioreactor before and/or during the fed-batch state. During the fed-batch state, the volume of the cell culture in the bioreactor grows while the cell concentration of the cell culture is maintained at a substantially constant level. This is illustrated as Step 2 in FIGS. 10A and 10B.

FIG. 9C illustrates a perfused batch state of operation in which the perfusion device 226 is turned on or operated to retain cells within the bioreactor, one or more medium inlet ports 202, 204, 212 of the bioreactor 200 are opened (so that cell growth medium is introduced into the bioreactor), an outlet port 228 of the bioreactor 200 is opened one or more times or continually (so that spent medium, which may contain biologicals of interest is harvested), and the fluid flows are controlled in real-time to maintain the culture volume at a substantially constant level. A sensor 238 detecting the culture volume, culture liquid level and/or culture liquid weight may be used to detect the culture volume in real-time by the control device 240 in order to determine, in real-time, the fluid flow that is needed to maintain the volume at a substantially constant level. Any suitable mechanism may be used to control the medium flow including, but not limited to, a flow control mechanism 214, 216, 224 provided at the medium inlet port 202, 204, 212, a flow control valve 230 provided at the outlet port 228, a rate of perfusion of the perfusion device 226, and the like. During the perfused-batch state, the cell concentration of the cell culture in the bioreactor grows while the volume of the cell culture is maintained at a substantially constant level. The perfusion flow rate may be controlled automatically in real-time to respond to the specific demands of the system, e.g., desired antibody secretion, desired viability, metabolic rate, and the like. This is illustrated as Step 3 in FIGS. 10A and 10B. If the targeted biological product (e.g., recombinant protein product) is prone to instability, the product may be harvested from the bioreactor. Proteins obtained in this step are typically biologically consistent with fewer glycosylation variations.

FIG. 9D illustrates a perfused fed-batch state of operation in which the perfusion device 226 is turned on or operated to retain cells within the bioreactor, one or more medium inlet ports 202, 204, 212 of the bioreactor 200 are opened (so that cell growth medium is introduced into the bioreactor), an outlet port 228 of the bioreactor 200 is opened one or more times or continually (so that spent medium, which may contain biologicals of interest, is harvested), and the fluid flows are controlled in real-time to maintain the cell concentration of the culture at a substantially constant level. A cell concentration probe or sensor 238 may be used to detect the viable cell density in real-time by the control device 240 in order to determine, in real-time, the fluid flow that is needed to maintain the cell concentration at a substantially constant level. The rate of perfusion may be adjusted automatically in real-time to the total number of cells. Any suitable mechanism may be used to control the medium flow including, but not limited to, a flow control mechanism 214, 216, 224 provided at the medium inlet port 202, 204, 212, a flow control valve 230 provided at the outlet port 228, a rate of perfusion of the perfusion device 226, and the like. In some embodiments, a growth limiting nutrient may be introduced into the bioreactor before and/or during the perfused fed-batch state. During the perfused fed-batch state, the volume of the cell culture in the bioreactor grows while the cell concentration of the cell culture is maintained at a substantially constant level. This is illustrated as Step 4 in FIGS. 10A and 10B.

FIG. 9E illustrates a cytostat state of operation in which the perfusion device 226 is turned on or operated continually, one or more medium inlet ports 202, 204, 212 of the bioreactor 200 are opened (so that cell growth medium is introduced into the bioreactor), an outlet port 228 of the bioreactor 200 is opened one or more times or continually (so that spent medium, which may contain biologicals of interest, is harvested), and the fluid flows are controlled in real-time to maintain the volume of the culture at a substantially constant level. A sensor detecting the culture volume, culture liquid level and/or culture liquid weight may be used to detect the culture volume in real-time by the control device 240 in order to determine, in real-time, the fluid flow that is needed to maintain the volume at a substantially constant level. Any suitable mechanism may be used to control the medium flow including, but not limited to, a flow control mechanism 214, 216, 224 provided at the medium inlet port 202, 204, 212, a flow control mechanism 230 provided at the outlet port 228, a rate of perfusion of the perfusion device 226, and the like.

In one embodiment in the cytostat state, a bleeding port 234 of the bioreactor 200 may be opened to remove cells from the bioreactor via flow control mechanism 236. In this embodiment, the cell concentration of the cell culture in the bioreactor may be kept substantially constant while the volume of the cell culture also remains substantially constant. The rate of perfusion may be adjusted automatically in real-time to the total number of cells. This is illustrated as Step 5 in FIGS. 10A and 10B.

In another embodiment in the cytostat state, a bleeding port 234 of the bioreactor 200 may be shut off or closed to prevent bleeding of cells. In this embodiment, the cell concentration of the cell culture in the bioreactor grows while the volume of the cell culture remains substantially constant. This is illustrated as Step 5 in FIGS. 10A and 10B.

In one exemplary embodiment illustrated in FIGS. 10A and 10B, a bioreactor (central/nurse and/or peripheral) may be operated in the following sequence of operational states: batch, fed-batch, perfused batch, perfused fed-batch and cytostat. In another exemplary embodiment, a bioreactor (central/nurse and/or peripheral) may be operated in the following sequence of operational states: batch, perfused batch and cytostat. One of ordinary skill in the art will recognize that any suitable sequence of operational states may be selected and used. In some embodiments, an operational sequence may include multiple instances of the same operational state (e.g., perfused batch followed by perfused fed-batch followed by perfused batch).

One or more pre-programmed or pre-configured control devices may be used to automatically establish the operational states in a bioreactor and to operate the bioreactor in a predefined sequence of operational states. The control device may automatically and, in real-time, determine when it is appropriate to transition from one operational state to another operational state by monitoring one or more operational conditions and comparing them to one or more predefined thresholds. These operational conditions may include, but are not limited to, viable cell density and/or cell culture volume.

Figure 11A:
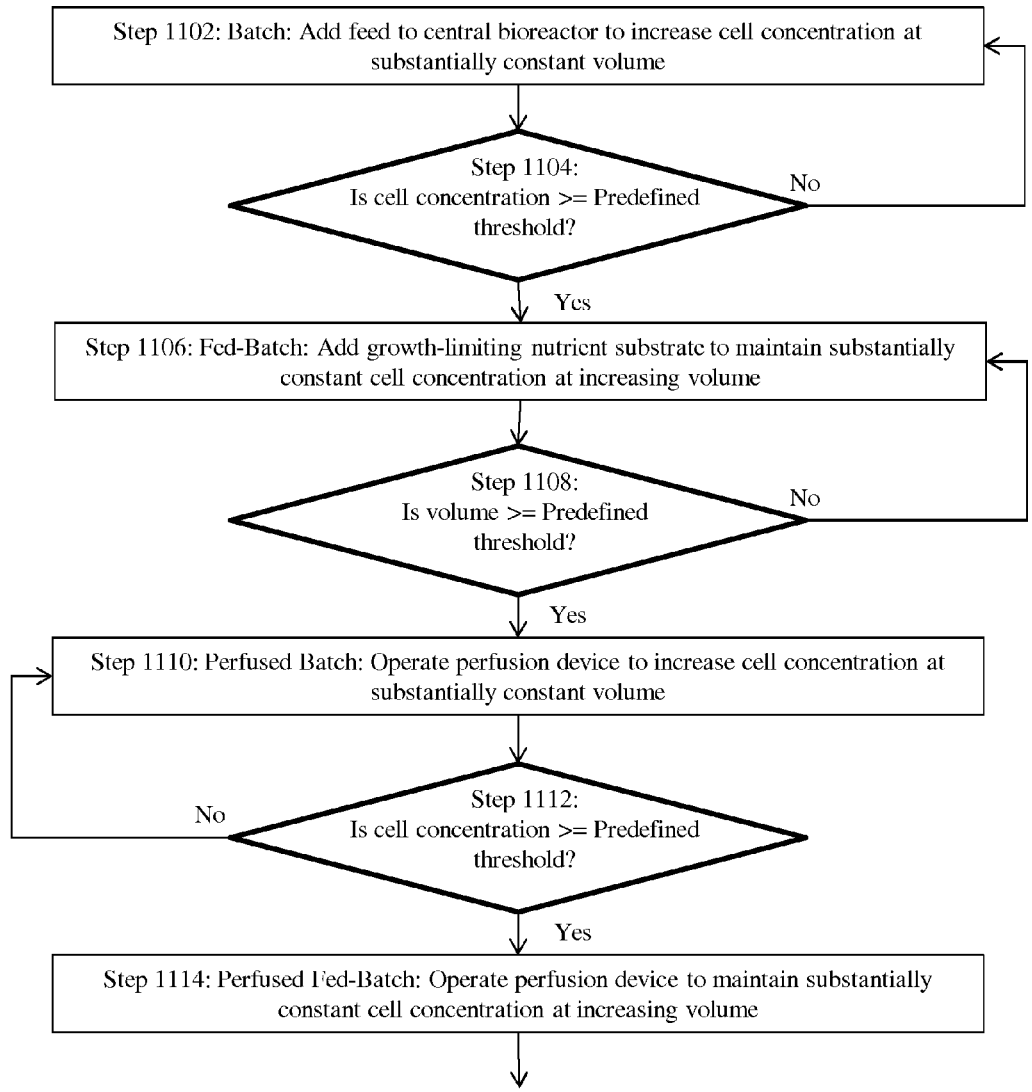
FIGS. 11A and 11B are flowcharts illustrating an exemplary method of operation of a bioreactor including batch, fed-batch, perfused batch, perfused fed-batch and perfusion operational states.
Figure 11B:
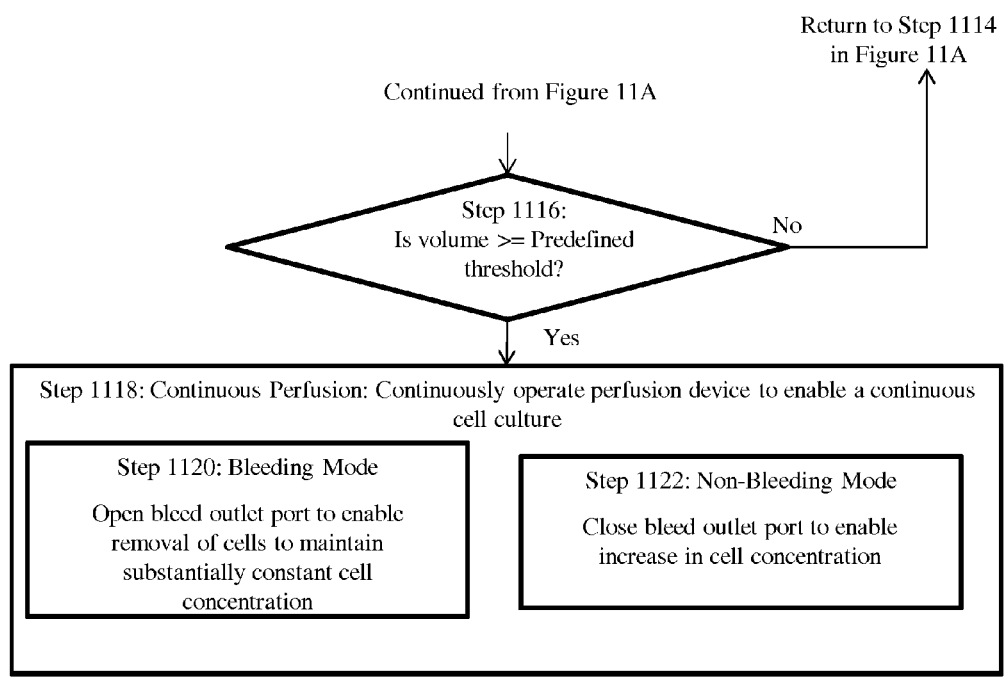

FIGS. 11A-11B are flowcharts illustrating the exemplary automatic operation shown in FIGS. 10A and 10B in which a bioreactor (central/nurse and/or peripheral) may be operated by a remote or local control device in the following sequence of operational states: batch, fed-batch, perfused batch, perfused fed-batch and cytostat. At any given time, the different bioreactors in an exemplary distributed system may be operating in the same operational state or in different operations states independently from one another.

In the batch step 1102 (illustrated as Step 1 in FIGS. 10A and 10B), a cell growth medium is added to the bioreactor at one or more discrete time points. The medium inlet port and medium outlet port are closed or shut off automatically (using, for example, a control device) to maintain the culture volume at a substantially constant level, while the cell concentration rises due to cell growth. The viable cell density is detected using a cell concentration probe, periodically or continually.

In step 1104, the viable cell density is programmatically compared to a first predefined cell density threshold (SP1* in FIG. 10B). This threshold (SP1* in FIG. 10B) constitutes a transition point between the batch state and the fed-batch state. If it is determined that the viable cell density has not reached the first cell density threshold, then operation continues in the batch step 1102. If, on the other hand, it is determined that the viable cell density is equal to or greater than the first cell density threshold, then operation proceeds to the fed-batch step 1106.

In the fed-batch step 1106 (illustrated as Step 2 in FIGS. 10A and 10B), the perfusion device is turned off, a medium inlet port of the bioreactor is opened (so that cell growth medium is introduced into the bioreactor), and the introduction of the medium is controlled by a control device, in real-time, to maintain the cell concentration at a substantially constant level. A cell concentration probe or sensor may be used to detect the viable cell density in real-time in order to determine, in real-time, the fluid flow that is needed to maintain the cell concentration at a substantially constant level. In some embodiments, a growth limiting nutrient may be introduced into the bioreactor before and/or during the fed-batch state.

In step 1108, the cell culture volume is programmatically compared to a first predefined volume threshold (SP1* in FIG. 10A). This threshold (SP1* in FIG. 10A) constitutes a transition point between the fed-batch state and the perfused batch state. If it is determined that the cell culture volume has not reached the first volume threshold, then operation continues in the fed-batch step 1106. If, on the other hand, it is determined that the cell culture volume is equal to or greater than the first volume threshold, then operation proceeds to the perfused batch step 1110.

In the perfused batch step 1110 (illustrated as Step 3 in FIGS. 10A and 10B), the perfusion device is turned on or operated, the medium inlet port of the bioreactor is opened (so that cell growth medium is introduced into the bioreactor), a medium inlet port of the bioreactor is opened one or more times or continually (so that spent medium, which may contain biologicals of interest, is harvested), and the fluid flows are controlled in real-time to maintain the culture volume at a substantially constant level. A sensor detecting the culture volume, culture liquid level and/or culture liquid weight may be used to detect the culture volume in real-time in order to determine, in real-time, the fluid flow that is needed to maintain the volume at a substantially constant level. Any suitable mechanism may be used to control the medium flow including, but not limited to, a flow control valve provided at the medium inlet port, a flow control valve provided at the perfusion device, a rate of perfusion used by the perfusion device.

In step 1112, the viable cell density is programmatically compared to a second predefined cell density threshold (SP2* in FIG. 10B). This threshold (SP2* in FIG. 10B) constitutes a transition point between the perfused batch state and the perfused fed-batch state. If it is determined that the viable cell density has not reached the second cell density threshold, then operation continues in the perfused batch step 1110. If, on the other hand, it is determined that the viable cell density is equal to or greater than the second cell density threshold, then operation proceeds to the perfused fed-batch step 1114.

In the perfused fed-batch step 1114 (illustrated as Step 4 in FIGS. 10A and 10B), the perfusion device is turned on or operated, the medium inlet port of the bioreactor is opened (so that cell growth medium is introduced into the bioreactor), a medium inlet port of the bioreactor is opened one or more times or continually (so that spent medium, which may contain biologicals of interest, is harvested), and the fluid flows are controlled in real-time to maintain the cell concentration of the culture at a substantially constant level. In some embodiments, one or more additional inlet ports may also be opened to introduce other materials into the bioreactor via corresponding flow control valves. A cell concentration probe or sensor may be used to detect the viable cell density in real-time in order to determine, in real-time, the fluid flow that is needed to maintain the cell concentration at a substantially constant level. Any suitable mechanism may be used to control the medium flow including, but not limited to, a flow control valve provided at the medium inlet port, a flow control valve provided at the perfusion device, a rate of perfusion used by the perfusion device. In some embodiments, a growth limiting nutrient may be introduced into the bioreactor before and/or during the perfused fed-batch state.

In step 1116, the cell culture volume is programmatically compared to a second predefined volume threshold (SP2* in FIG. 10A). This threshold (SP2* in FIG. 10A) constitutes a transition point between the perfused fed-batch state and the cytostat state. If it is determined that the cell culture volume has not reached the second volume threshold, then operation continues in the perfused fed-batch step 1114. If, on the other hand, it is determined that the cell culture volume is equal to or greater than the second volume threshold, then operation proceeds to the cytostat step 1118.

In the cytostat step 1118 (illustrated as Step 5 in FIGS. 10A and 10B), the perfusion device is turned on or operated continually, the medium inlet port of the bioreactor is opened (so that cell growth medium is introduced into the bioreactor), a medium inlet port of the bioreactor is opened one or more times or continually (so that spent medium, which may contain biologicals of interest, is harvested), and the fluid flows are controlled in real-time to maintain the volume of the culture at a substantially constant level. In some embodiments, one or more additional inlet ports may also be opened to introduce other materials into the bioreactor via corresponding flow control valves. A sensor detecting the culture volume, culture liquid level and/or culture liquid weight may be used to detect the culture volume in real-time in order to determine, in real-time, the fluid flow that is needed to maintain the volume at a substantially constant level. Any suitable mechanism may be used to control the medium flow including, but not limited to, a flow control valve provided at the medium inlet port, a flow control valve provided at the perfusion device, a rate of perfusion used by the perfusion device.

In one embodiment in the cytostat state illustrated in sub-step 1120, a cell outlet port of the bioreactor may be opened to bleed out cells via flow control valve. In this embodiment, the cell concentration of the cell culture in the bioreactor remains substantially constant while the volume of the cell culture also remains substantially constant. This sub-step is illustrated as "with bleeding" in FIG. 10B.

In another embodiment in the cytostat state illustrated in sub-step 1122, a cell outlet port of the bioreactor may be closed off to prevent bleeding of cells. In this embodiment, the cell concentration of the cell culture in the bioreactor grows while the volume of the cell culture remains substantially constant. This sub-step is illustrated as "no bleeding" in FIG. 10B.

One of ordinary skill in the art will recognize that any suitable numerical values or numerical ranges may be set as the SP1* and SP2* threshold indicated in FIGS. 10A and 10B based on, for example, the cell line being developed and the cell culture media.

IV. Exemplary Bioreactor Control Computing Devices

Figure 12:
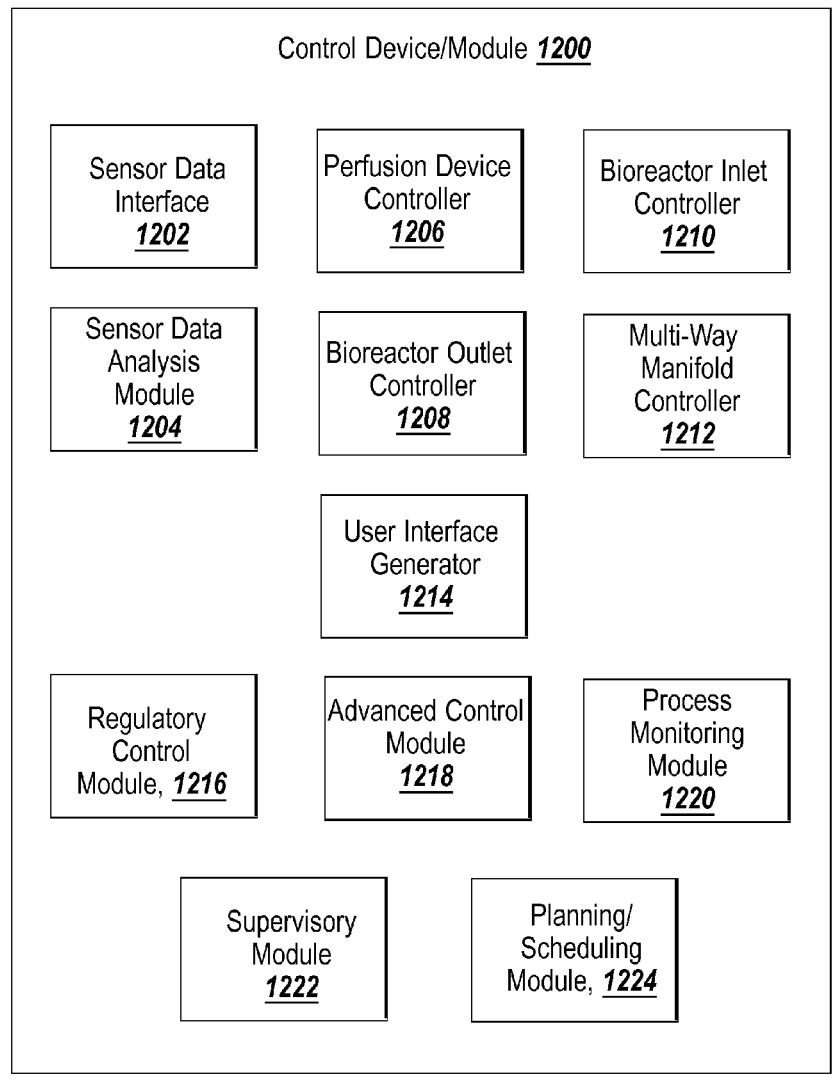
FIG. 12 is a block diagram illustrating exemplary modules in a bioreactor control device used in the operation of an exemplary bioreactor.

FIG. 12 is a block diagram of an exemplary bioreactor control device or module 1200 that is programmed or configured to automatically control one or more bioreactors and other components in a distributed bioreactor system. One of ordinary skill in the art will recognize that the modules illustrated in FIG. 12 are illustrative and are not meant to limit the scope of the invention. For example, the structure, operation and function embodied in the modules may be split across more modules or may be consolidated within fewer modules than those illustrated.

The control device 1200 may include a sensor data interface 1202 programmed or configured to programmatically receive data from one or more sensors or probes in a bioreactor, e.g., cell concentration probe, volume sensor, and the like. The control device 1200 may include a sensor data analysis module 1204 programmed or configured to programmatically analyze the received sensor data, for example, to determine a viable cell density (based on a capacitance data), to compare data to predefined thresholds, and the like. In some embodiments, the sensor data analysis module 1204 may perform multivariate statistical analysis of data, for example, to determine the density of metabolically active cells.

In some embodiments, one or more types of sensor data may be analyzed by the sensor data analysis module 1204 to control removal of waste, e.g., lactic acid and ammonia produced by the cultured cells. The sensor data analysis module 1204 may use data from or may control online or at-line reverse electro-enhanced dialysis (REED) technology obtained from JURAG (http://www.jurag.dk, the entire contents of which are incorporated herein by reference), in some embodiments. When integrated to fermentation processes, Jurag's REED technology can separate small molecular compounds from a broth helping to control and improve the microbial growth processes. In some embodiments, the sensor data analysis module 1204 may use online or at-line measurements of stable-isotopic composition of gases in the bioreactor, for example, using continuous flow isotope-ratio mass spectrometry. In some embodiments, the sensor data analysis module 1204 may use quality information from early-stage downstream operations, for example, quality or related information from the secreted or by-products targeted. In some embodiments, the sensor data analysis module 1204 may implement "counter measure" strategies to improve control of the perfusion process and its profile to predict, at an early-stage, any process deviation or contamination of the cultured cells and targeted productivity from batch to batch.

The control device 1200 may include a perfusion device controller 1206 programmed or configured to automatically turn on/off a perfusion device and to control a rate of the perfusion device. The control device 1200 may include a bioreactor outlet controller 1208 programmed or configured to automatically open/close one or more outlet ports at a bioreactor and to control flow rates at the outlet ports. The control device 1200 may include a bioreactor inlet controller 1210 programmed or configured to automatically open/close one or more inlet ports at a bioreactor and to control flow rates at the inlet ports. The control device 1200 may include a multi-way manifold controller 1212 programmed or configured to automatically control the open/close states of the manifold to sequentially feed a cell culture from a central bioreactor to a plurality of peripheral bioreactors and to control flow rates at the manifold.

The control device 1200 may include a user interface generator 1214 programmed or configured to render a user interface on a visual display device. The user interface may display or otherwise provide information regarding operation of the bioreactor system to a user, and/or may receive input from a user to affect operation of the bioreactor system. A user may need to be trained to use the interface a single time and would not need extensive and expert training in the operation of bioreactors in order to monitor the automatic operation of the system.

In some embodiments, the control device 1200 may include one or more of the following modules:

A regulatory control module 1216 is programmed or configured to perform the control mechanisms illustrated in FIGS. 11A and 11B. For example, the regulatory control module 1216 is programmed or configured to provide an automatic feedback control function for tracking and regulating operational parameters (e.g., cell concentration, cell culture volume, pH, dissolved oxygen, temperature, agitation rate, gas flow rate, medium flow rate, and the like). The regulatory control 1216 may obtain real-time data on the operational parameters using any suitable mechanism, for example, capacitance probes, volume sensors, and the like. The regulator control module 1216 may, for example, compare an operational parameter (e.g., cell concentration and/or culture volume) to one or more predetermined thresholds (e.g., SP1* and SP2* in FIGS. 10A and 10B) and, based on the comparison, may automatically control an operational characteristic of the bioreactor system to achieve a desired condition or status. For example, the regulator control module 1216 may control a flow rate of the cell culture medium flowing into or out of a bioreactor, a perfusion rate, and the like.

An advanced control module 1218 programmed or configured to automatically perform improved control and predictive functions to allow improved and more precise control performance. An exemplary advanced control module 1218 may use, e.g., feed-forward, cascade, multi-loop predictive multivariate models, and the like. The advanced control module also controls the perfusion rate, and performs feed compensation, product quality control and productivity control.

In some embodiments, the advanced control module 1218 may employ a multivariate statistical model to predict productivity and/or product quality. The statistical model may be trained and developed based on historical data of off-line measurements of bioreactor conditions (e.g., raw material quality, inoculum condition, and the like). The trained model may be used on online measurements to predict the productivity and/or the product quality (e.g., titer, glycosylation of the protein, and the like). Product and quality estimations may also be based on soft-sensor models that are based on data from bioreactor sensors. The predictions may be used to perform mid-course corrections of the bioreactor operation to achieve a desired productive and/or a desired final product quality of the biological products (e.g., antibodies, recombinant proteins, and the like).

A process monitoring module 1220 programmed or configured to automatically perform multivariate analysis of operational parameters, and to monitor and diagnose in real-time process deviations, contamination and other abnormalities. The process monitoring module 1220 may be used to monitor the current status of each of the bioreactors separately or all the currently running bioreactors together in a distributed perfusion system. In some embodiments, a training system may be used to train the process monitoring module 1220 using normal historical data so that the module can use multivariate analysis to determine common-cause process variations. The trained model may be used on online measurements to detect or predict any abnormalities in the process. The detection or prediction of abnormalities may be used to perform mid-course corrections of the bioreactor operation to correct for the abnormalities. The process monitoring may be based on, but is not limited to, PCA (Principal Component Analysis), PLS (Partial Least Square), PLS-DA (Partial Least Square-Discriminant Analysis) methods, and the like.

A supervisory module 1222 programmed or configured to operate a bioreactor system, for example, to minimize operating cost, maximize profit, minimize utility consumption, and the like. In some embodiments, the supervisory module may use predefined pH and dissolved oxygen thresholds to control system operation. In some embodiments, the supervisory module 1222 (e.g., model predictive control and the like) may make an automatic or manual decision to adapt one or more operational conditions of the bioreactor system (e.g., using modules 1216, 1218, 1220 and the like) to achieve a desired condition or specification in the system.

A planning and scheduling module 1224 programmed or configured to operate a bioreactor system based on strategic operating considerations based on plant supply chain management (e.g., the production rate). In some embodiments, the planning and scheduling module 1224 (e.g., real-time optimizer and the like) may automatically determine a production plan based, for example, on availability of raw material components, manufacturing facility constraints, demand or need for drug substances, and the like. The production plan may be based on achieving plant objectives, such as, maximum throughput, minimum utilities/raw material usage, maximum plant efficiency, and the like. The constraints and desired objectives may be converted into mathematical problems which are solved by the planning and scheduling module 1224 using optimization programming tools.

Figure 13:
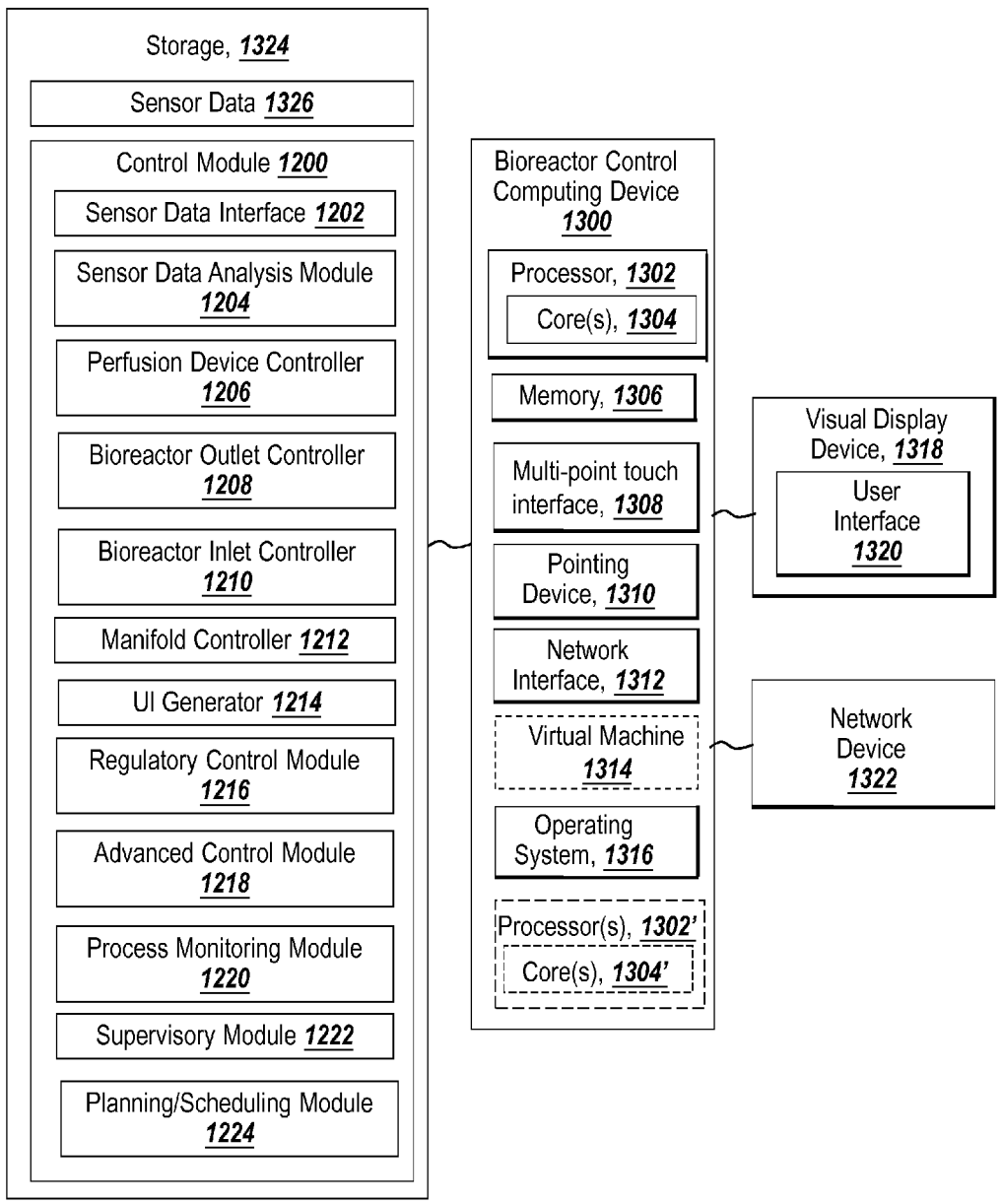
FIG. 13 is a block diagram illustrating an exemplary bioreactor control computing device.

FIG. 13 is a block diagram of an exemplary bioreactor control computing device 1300 that may be used to perform any of the methods or implement any of the systems and devices provided by exemplary embodiments. The computing device 1300 includes one or more non-transitory computer-readable media for storing one or more computer-executable instructions or software for implementing exemplary embodiments. The non-transitory computer-readable media may include, but are not limited to, one or more types of hardware memory, non-transitory tangible media, and the like. For example, memory 1306 included in the computing device 1300 may store computer-executable instructions or software for implementing exemplary embodiments. In one embodiment, memory 1306 may include a control module 1200 for storing computer-readable data and computer-executable instructions that implement and perform methods associated with controlling operation of one or more bioreactors. Memory 1306 may include a computer system memory or random access memory, such as DRAM, SRAM, EDO RAM, and the like. Memory 1306 may include other types of memory as well, or combinations thereof.

The computing device 1300 includes processor 1302 and, optionally, one or more additional processor(s) 1302' for executing computer-executable instructions or software stored in the memory 1306 and one or more other programs for controlling system hardware. Processor 1302 and optional processor(s) 1302' may each be a single core processor or multiple core (1304 and 1304') processor. Virtualization may be employed in the computing device 1300 so that infrastructure and resources in the computing device may be shared dynamically. A virtual machine 1314 may be provided to handle a process running on multiple processors so that the process appears to be using only one computing resource rather than multiple computing resources. Multiple virtual machines may also be used with one processor.

A user may interact with the computing device 1300 through a visual display device 1318, such as a computer monitor, which may display one or more user interfaces 1320 or any other interface.

The computing device 1300 may include other I/O devices such a keyboard or a multi-point touch interface 1308 and a pointing device 1310, for example a mouse, for receiving input from a user. The keyboard 1308 and the pointing device 1310 may be connected to the visual display device 1318. The computing device 1300 may include other suitable conventional I/O peripherals. The computing device 1300 may also include a storage device 1324, such as a hard-drive, CD-ROM, or other computer readable media, for storing data and computer-readable instructions or software that implement exemplary embodiments.

In one embodiment, the storage device 1324 may include sensor data 1326 and a control module 1200 for storing data and computer-readable instructions that implement and perform methods associated with controlling operation of one or more bioreactors.

The computing device 1300 may include a network interface 1312 configured to interface via one or more network devices 1322 with one or more networks, for example, Local Area Network (LAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, controller area network (CAN), or some combination of any or all of the above. The network interface 1312 may include a built-in network adapter, network interface card, PCMCIA network card, card bus network adapter, wireless network adapter, USB network adapter, modem or any other device suitable for interfacing the computing device 1300 to any type of network capable of communication and performing the operations described herein. Moreover, the computing device 1300 may be any computer system, such as a workstation, desktop computer, server, laptop, handheld computer or other form of computing or telecommunications device that is capable of communication and that has sufficient processor power and memory capacity to perform the operations described herein.

The computing device 1300 may run any operating system 1316, such as any of the versions of the Microsoft® Windows® operating systems, the different releases of the Unix and Linux operating systems, any version of the MacOS® for Macintosh computers, any embedded operating system, any real-time operating system, any open source operating system, any proprietary operating system, any operating systems for mobile computing devices, or any other operating system capable of running on the computing device and performing the operations described herein. The operating system 1316 may be run in native mode or emulated mode. In an exemplary embodiment, the operating system 1316 may be run on one or more cloud machine instances.

Figure 14:
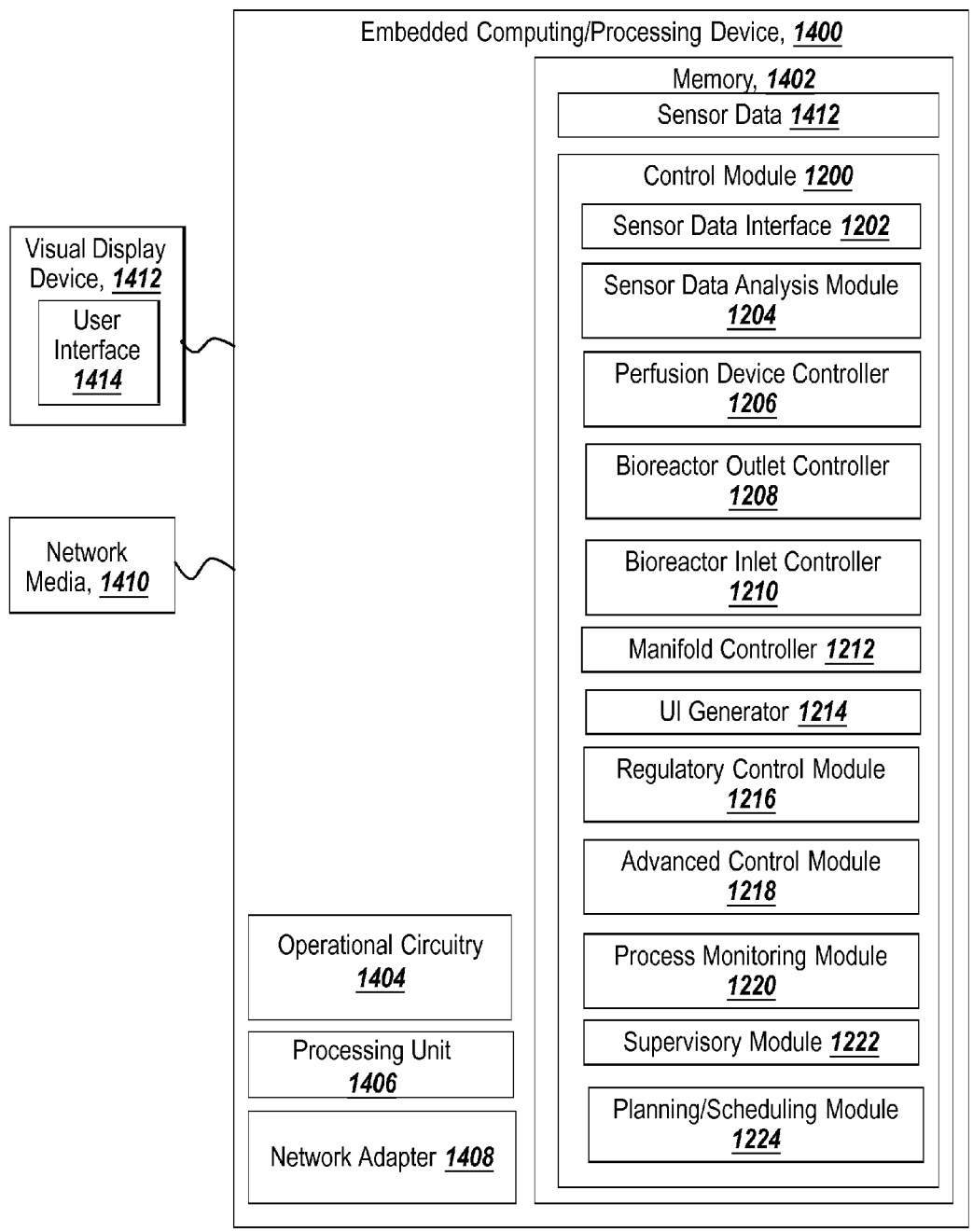
FIG. 14 is a block diagram illustrating an exemplary embedded bioreactor control computing device.

Exemplary methods may be implemented and executed on one or more embedded computing devices. FIG. 14 is a block diagram of an exemplary embedded bioreactor control computing or processing device 1400 that may be used to perform any of the methods or implement any of the systems and devices provided by exemplary embodiments. The embedded computing device 1400 may be any suitable device incorporating electronics to control operational functions, and in which computing and networking capabilities are embedded. For example, devices in which the computing and networking capabilities may be embedded may include, but are not limited to, bioreactor control hardware equipment, audio-video equipment (e.g., audio and video recorders and players, televisions, digital cameras, digital video cameras, compact disks, digital video disks, camcorders, and the like), communication devices (e.g., telephones, cell phones, audio and video conferencing systems, the iPhone™ communication device, the iPad™ communication device, and the like), and the like.

The embedded computing device 1400 may include memory 1402 that includes one or more non-transitory computer-readable media for storing one or more computer-executable instructions or software for implementing exemplary embodiments. The non-transitory computer-readable media may include, but are not limited to, one or more types of hardware memory, non-transitory tangible media, and the like. Memory 1402 may include a computer system memory or random access memory, such as DRAM, SRAM, EDO RAM, and the like. Memory 1402 may include other types of memory as well, or combinations thereof. In one embodiment, memory 1402 may include sensor data 1412 and a control module 1200 for storing data and computer-readable instructions that implement and perform methods associated with controlling operation of one or more bioreactors.

The embedded computing device 1400 may include operational circuitry 1404 that operate device functions. The embedded computing device 1400 may include one or more processing units 1406 to provide embedded computing capabilities. The processing unit 1406 may execute computer-executable instructions or software for implementing exemplary embodiments, and one or more other programs for controlling system hardware. The processing unit 1406 may have hardware interfaces to the operational circuitry 1404 that operate device functions. The processing unit 1406 may be one or more microprocessors or one or more micro-controllers.

A user may interact with the computing device 1400 through a visual display device 1412, such as a computer monitor, which may display one or more user interfaces 1414 or any other interface.

The embedded computing device 1400 may include one or more network adapters 1408 for connecting with a network media 1410 that is interconnected with a computer network. The network adapter 1408 may be a network interface card suitable to the particular network media 1410. For example, exemplary network adapters 1408 may include, but are not limited to, a built-in network adapter, network interface card, PCMCIA network card, card bus network adapter, wireless network adapter, USB network adapter, modem or any other device. The network media 1410 may be any type of wired or wireless network media including, but not limited to, Ethernet, firewire, radio frequency, television cable, Local Area Network (LAN), Wide Area Network (WAN) or the Internet through a variety of connections including, but not limited to, standard telephone lines, LAN or WAN links (for example, 802.26, T1, T3, 56 kb, X.25), broadband connections (for example, ISDN, Frame Relay, ATM), wireless connections, controller area network (CAN), or some combination of any or all of the above.

V. Exemplary Targeted Biological Products Produced Using Exemplary Bioreactor Systems A cell culture produced and maintained using exemplary bioreactor systems may be used to produce any suitable targeted biological product. In one embodiment, a cell culture may be produced and maintained to manufacture a targeted recombinant protein. Exemplary targeted recombinant proteins may include, but are not limited to, antibodies, a biologically targeted product thereof, and the like.

In some embodiments, the cell culture produces a protein, e.g., a recombinant protein. A recombinant protein is produced using recombinant DNA technology that allows cells, e.g., bacterial cells, yeast cells or mammalian cells, to produce heterologous proteins, i.e., proteins not normally synthesized by these cells. Genetic engineering allows high expression of the gene coding the protein of interest using vectors that are designed to replicate foreign DNA, and control transcription and translation of the introduced gene.

As used herein, the "recombinant protein" includes any protein, peptide or a polypeptide that may be produced recombinantly, e.g., a protein, peptide or a polypeptide for which the corresponding gene sequence is known. A recombinant protein may be derived from any organism, e.g., a prokaryotic organism, such as bacteria, or an eukaryotic organism, such as yeast or a mammal, e.g., a rat, a mouse, a pig, a horse or a human. In one embodiment, the recombinant protein is derived from a human.

In some embodiments, a "recombinant protein" is a protein, a peptide or a polypeptide useful for research purposes. A catalogued list of such proteins, peptides and polypeptides may be found, e.g., in product catalogues of any company that sells proteins, peptides and polypeptides for research purposes, e.g., in Sigma-Aldrich product catalog, Life Technologies product catalog, New England Biolabs product catalog, and the like. Non-limiting examples of such recombinant proteins, peptides and polypeptides include enzymes, e.g., restriction endo- and exonucleases, DNA polymerases, DNA repair enzymes, such as DNA glycosylases; DNA binding proteins, such as transcription factors; cell receptors, such as insulin receptor and VEGF receptor; cytokines, such as interleukins; growth factors and hormones, such as insulin; cytoskeleton and extracellular matrix proteins, such as actin; apoptosis proteins, such as caspases; chaperonins; G proteins; heat shock and related proteins; immune system proteins, including antibodies specific to any protein, such as any protein listed herein; neural proteins, such as myelin, oxidative stress proteins, such as glutathione reductase or catalase; and ubiquitin.

In some embodiments, a "recombinant protein" is a protein, peptide or a polypeptide useful for diagnostic, therapeutic or prophylactic purposes, e.g., for diagnosing, treating or preventing a disease or a condition in a subject, e.g., a human. The term "recombinant protein", therefore, includes any protein, peptide or a polypeptide with enzymatic or regulatory activity that functions to replace a protein that is deficient or abnormal; any protein, peptide or polypeptide that functions to augment an existing pathway or to provide a novel function or activity; any protein, peptide or polypeptide that functions to interfere with a molecule or an organism, and any protein, peptide or polypeptide that functions to deliver other compounds of proteins (Leader et al., *Nature Reviews Drug Discovery* (2008), 7:21-39). The term "recombinant protein" also includes proteins, peptides and polypeptides that may be used for diagnostics or imaging, or for producing vaccines for protecting a subject, e.g., a human, against a deleterious foreign agent, e.g., a virus or bacteria, to treat an autoimmune disease or to treat cancer.

Non-limiting examples of proteins, peptides and polypeptides useful for therapeutic, diagnostic or prophylactic purposes include, but are not limited to:

hormones and proteins, peptides and polypeptides useful for treating endocrine deficiencies and for regulating growth, e.g., insulin, growth hormone (GH), recombinant insulin-like growth factor 1 (IGF1), calcitonin, teriparatide (parathyroid hormone), exenatide, octreotide, dibotermin-a (human bone morphogenic protein 2, rhBMP2), histrelin acetate (gonadropin releasing hormone, GnRH), palifermin (keratinocyte growth factor, KGF), becaplermin (platelet-derived growth factor, PDGF), glucagon, growth hormone releasing hormone (GHRH), secretin and thyroid stimulating hormone (TSH, thyrotropin);

proteins, peptides and polypeptides that function in homeostasis and thrombosis, e.g., Factor VIII, Factor IX, antithrombin III (AT-III), protein C, alterplase (tissue plasminogen activator, tPA), reteplase (deletion mutein of tPA), tenecteplase, urokinase, Factor VIIa, drotrecogin-α (activated protein C), lepirudin, bivalirudin, streptokinase and anistreplase (anisoylated plasminogen streptokinase activator complex, APSAC);

proteins, peptides and polypeptides useful for treating metabolic disorders, e.g., β-Gluco-cerebrosidase, algucosidase-α, Laronidase (α-I-iduronidase), idursuphase (iduronate-2-sulphatase), gasuphase and agalsidase-β;

proteins, peptides and polypeptides useful for treating pulmonary and gastrointestinal tract disorders, e.g., α-1-proteinase inhibitor, lactase and pancreatic enzymes, such as lipase, amylase and protease;

proteins, peptides and polypeptides useful for treating immunodeficiencies, e.g., adenosine deaminase (pegademase) or immunoglobulins and enfuvirtide (Fuzeon, a 36 amino acid peptide that inhibits HIV entry into host cells);

proteins, peptides and polypeptides functional in haemotopoiesis, e.g., erythropoietin, darbepoetin-α, filgrastim (granulocyte colony stimulating factor; G-CSF); sargramostim (granulocyte-macrophage colony stimulating factor, GM-CSF), oprelvekin (interleukin 11, IL11);

proteins, peptides and polypeptides useful for treating fertility disorders, e.g., follicle-stimulating hormone (FSH), chorionic gonadotropin (HCG) and lutropin-α;

proteins, peptides and polypeptides functional in immunoregulation; e.g., type I alpha-interferon, interferon-α2a, interferon-αn3 (IFNαn3), interferon-β 1a (rIFN-β), interferon-γ1b (IFNγ), interleukin 2 (IL2), abatacept (fusion protein between extracellular domain of human CTLA4 and the modified Fc portion of human immunoglobulin G1), interleukin 1 (IL1), etanercept (dimeric fusion protein between recombinant soluble TNF receptor and Fc portion of human immunoglobulin G1), alefacept (dimeric fusion that binds CD2 on the surface of lymphocytes and inhibits interaction with LFA3);

trypsin; nesiritide (B-type natriuretic peptide); albumin;

proteins, peptides and polypeptides that function as enzymes in degradation of macromolecules, e.g., bolulinum toxin type A, botulinum toxin type B, collagenase, human deoxy-ribonuclease I, hyaluronidase and papain;

proteins, peptides and polypeptides that function in degradation of small molecules, e.g., L-asparadinase and rasburicase;

proteins, peptides and polypeptides that are useful for transplantation, e.g., antithymocyte globulin;

crotalidae polyvalent immune Fab (Crofab, a mixture of Fab fragments of IgG that bind and neutralize venom toxins of ten clinically important North American Crotalidae snakes);

digoxin immune serum Fab (Digifab, monovalent Fab immunoglobulin fragment obtained from sheep immunized with a digoxin derivative);

denileukin diftitox (Ontak, directs the cytocidal action of diphtheria toxin to cells expressing the IL2 receptor);

proteins, peptides and polypeptides useful in treating autoimmune disorders, e.g., anti-rhesus (Rh) immunoglobulin G (Rhophylac);

proteins, peptides and polypeptides useful for producing vaccines, e.g., hepatitis B surface antigen (HBsAg), capsid proteins from HPV strains that are included in the HPV vaccine (Gardasil) and OspA (a lipoprotein on outer surface of *Borrelia burgdorferi*);

proteins, peptides and polypeptides useful for diagnostics and imaging, e.g., recombinant purified protein derivative (DPPD, a protein from *Mycobacterium tuberculosis*), indium-111-octreotide (OctreoScan), apcitide (Acutect), HIV antigens and hepatitis C antigens.

Recombinant proteins also include targeted proteins, peptides and polypeptides. In some embodiments, such targeted proteins peptides and polypeptides are antibodies or fragments thereof. In some embodiments, the antibodies are monoclonal antibodies or fragments thereof (mAbs) useful for treating and diagnosing diseases, e.g., cancer. Non-limiting examples of monoclonal antibodies and fragment thereof include bevacizumab (Avastin), Cetuximab (Erbitux), panitumumab (Vectibix), alemtuzumab (Campath), rituximab (Rituxan), trastuzumab (Herceptin), adalimumab (Humira), infliximab (Remicade), efalzumab (Raptiva), natalizumab (Tysabri), eculizumab (Soliris), basiliximab (Simulect), daclizumab (Zenapax), muromonab-CD3 (Orthoclone, OKT3), palivizumab (Synagis), abciximab (ReoPro), ranibizumab (Lucentis), ibritumomab tiuxetan (Zevalin), gemtuzumab ozogamicin (Mylotarg), tositumomab and $^{131}$I-tositumomab (Bexxar, Bexxar I-131), capromab pendetide (ProstaScint), satumomab pendetide (OncoScint), arcitumomab (CEA-scan), nofetumomab (Verluma), imciromab pentetate (Myoscint) and technetium fanolesomab (NeutroSpec).

The entire contents of all references, including patents, patent applications and non-patent publications, cited throughout this application are hereby incorporated herein by reference in their entirety. The appropriate components and methods of those references may be selected for the invention and embodiments thereof. Still further, the components and methods identified in the Background section are integral to this disclosure and may be used in conjunction with or substituted for components and methods described elsewhere in the disclosure within the scope of the invention.

In describing exemplary embodiments, specific terminology is used for the sake of clarity. For purposes of description, each specific term is intended to, at least, include all technical and functional equivalents that operate in a similar manner to accomplish a similar purpose. Additionally, in some instances where a particular exemplary embodiment includes a plurality of system elements or method steps, those elements or steps may be replaced with a single element or step. Likewise, a single element or step may be replaced with a plurality of elements or steps that serve the same purpose. Further, where parameters for various properties are specified herein for exemplary embodiments, those parameters may be adjusted up or down by 1/20th, 1/10th, 1/5th, 1/3rd, 1/2nd, and the like, or by rounded-off approximations thereof, unless otherwise specified. Moreover, while exemplary embodiments have been shown and described with references to particular embodiments thereof, those of ordinary skill in the art will understand that various substitutions and alterations in form and details may be made therein without departing from the scope of the invention. Further still, other aspects, functions and advantages are also within the scope of the invention.

Exemplary flowcharts are provided herein for illustrative purposes and are non-limiting examples of methods. One of ordinary skill in the art will recognize that exemplary methods may include more or fewer steps than those illustrated in the exemplary flowcharts, and that the steps in the exemplary flowcharts may be performed in a different order than shown.

The present disclosure will be further described with respect to the following examples; however, the scope of the disclosure is not limited thereby.

Example 1

Perfusion, when it's well managed, generally offers many economical and performance advantages. Unfortunately, perfusion is sometimes perceived as being too complex, perfusion devices are thought to be too expensive and likely to clog, and seen to be risky for contamination. The achievement of higher productivity without a costly investment, and the time consuming optimization of the process and scale-up can be seen as difficulties. Some in the industry currently believe that no process control can truly manage perfusion.

The exemplary systems and methods of present disclosure are a breakthrough for cell culture experts who believe in perfusion and scale-up of such model. From process development to production, the present disclosure proposes a different model where scale-up and its management difficulties are by-passed with a SOP model: Scale Out Perfusion model.

The utilization of the same equipment, same model, same process design from process development to continuous manufacturing at the commercial scale is discussed. A case study using SOP is demonstrated based on performances obtained with a commercial media and HeLa cells.

This innovative and unique method of perfusion control (SOP) leads to a new process development concept and manufacturing process design for mAbs and therapeutic proteins.

In general, the increasing demand for therapeutic and diagnostic protein is leading to a higher demand of productivity in production facilities. Greater productivity, lower cost and higher efficiencies of upstream processes in cell culture are improvements which have been naturally expected for several decades.

Usually for mammalian processes at large scale, batch and fed-batch bioreactors are used. Among the disadvantages of a batch model are the relatively low final cell density and a low volumetric productivity.

Perfusion cultures have been developed and extensively used as an effective means to achieve high densities of mammalian cells for producing various substances such as monoclonal antibodies, recombinant proteins and baculovirus. The perfusion culture model increases the volumetric productivity of the bioreactor being considered.

A perfused culture process is run continuously so equipment downtime is reduced when compared to batch and fed-batch processes. Continuous operations require smaller downstream equipment. Compared to fed-batch bioreactors, perfusion bioreactors have a smaller scale/size due to culturing cells at about 10×-30× concentrations compared with fed-batch bioreactors, with some operating at about 100× or greater. This size reduction makes perfusion more amenable to single-use applications. A disposable 50 L perfusion bioreactor could produce the same amount of product as a 1,000 L fed-batch bioreactor. Pilot-scale perfusion bioreactor systems can be expected to have outputs comparable to conventional production-scale batch and fed-batch bioreactors. With perfusion, less equipment supporting space, utilities, and labor are required. Thus, perfusion can provide considerable cost savings.

Running a perfusion process means substantially no accumulation of metabolic waste products in the bioreactor. Expressed proteins are rapidly removed and available for purification, which is a significant advantage with proteins prone to instability. The steady-state concentration of metabolites and the reduced product retention time in perfusion processes often has a beneficial influence on final product quality. The cost of a batch failure with perfusion also tends to be much lower. If contamination is found, earlier unaffected harvests are still usable; and if contamination occurs early, then relatively small amounts of media and effort are wasted. Conversely, the whole batch must be discarded with a fed-batch process. During a perfusion process, cells are growing more naturally with less shear stress. Perfusion is usually providing recombinant proteins/antibodies that are purer, more like native proteins and more consistent in their biological activities than with a fed-batch bioreactor, such as having fewer variations in glycosylation.

Acoustic Perfusion Principle:

The first acoustic separator used in a perfusion culture yielded a 70-fold increase in volumetric productivity compared to batch (Trampler et al., 1994) with mostly greater than 90% separation efficiency. Exposure of mammalian cells to MHz-range acoustic standing wave fields has no substantial impact on culture viability, glucose uptake rate, or antibody production.

Acoustic separators are relatively simple, reliable, and nearly maintenance-free, but their use has been limited to flow rates up to about 60 L/day for a 20 L perfusion device. Perfusion systems have the possibility to be operated continuously for several months.

During perfusion the medium is continuously refreshed, giving the possibility for long-term operation. In fed-batch systems the culture is harvested batch wise leading to a relatively short operation time and more downtime.

In general, there are no physical barriers or moving mechanical parts in acoustic perfusion, therefore, it is less prone to fouling, mechanical failure, shear and tangential stress. Acoustic cell separation is based on pressure differences caused by the acoustic standing waves in the resonator chamber. As a result, the cells move to the pressure nodes where they accumulate, and settle down, creating a cell-free supernatant. This method is preferable for some unstable proteins since the cell-free supernatant containing the product of interest is continuously removed from the bioreactor.

Scale-Free or the Scale-Out Perfusion Model Principle:

Upstream scale-up is a complex engineering task needing expertise and fine-tuning of bioreactor design and operational configuration to enable the targeted productivity at the scale considered. Before large-scale commercial manufacturing can be implemented, it is typically necessary to scale up a set of different bioreactor volumes during a process development stage. However, conventional scale-up models have some technical challenges and financial risks. Conventional bioprocess engineering involves many steps of volume increases using different volumes, agitation, ratio, and finally different mass transfer models. Scaled process when its transferred to manufacturing involves a lot of engineering labor as mass transfer tends to cause reduction in performance. Due to variability in operational and performance at each scale-up step, it is also challenging to satisfy regulatory and safety requirements using a conventional scale-up. Furthermore, in conventional scale-up, bioreactor components should be sterilized at each scale-up step so finally another source of issues as contamination forcing to stop the manufacturing.

The scale out perfusion model is a distributed set of perfused bioreactors in which pluralities of modular, independent but similar perfused bioreactors are operated in parallel to produce and maintain a biological cell culture. A central perfused bioreactor (also called the feeder) produces and maintains a cell culture and transfers portions of the cell culture to the peripheral perfused bioreactors, each of which produces and maintains independently the cell culture in distinctive turn. Each peripheral bioreactor is similar to each other with a plug and play configuration that may be plugged to the feeder to scale out the process without increasing the scale of a process. This method will limit contamination issues and facilitate the segregation of a particular peripheral bioreactor without stopping manufacturing. The process is configured such that one-way fluid communication is established from the feeder to each of the peripheral bioreactors while maintaining fluid isolation among the peripheral bioreactors. Such scale-free model may be configured to maintain the cell culture continuously for extended periods of time.

At any given time, the different bioreactors in the distributed system may be operating in the same or different operational states.

Sterility may be achieved partially or totally using any suitable technique (e.g., gamma irradiation). In some processes, feeder and all peripheral bioreactors are sterilized together to simplify start-up, operation and exchanges of a peripheral bioreactor. The exchange of a peripheral bioreactor may be performed anytime using sterile connectors or such alike technique. Coupling at any time an additional similar peripheral bioreactor to the feeder increases the overall productivity of the complete perfused platform. The modularity of the scale free perfusion model enables a scale out design of an exemplary qualified bioreactor system during process development that avoids the disadvantages of a conventional scale-up model.

Adding the same peripheral bioreactor to a feeder to increase manufacturing productivity is efficient without having to retest, qualify or reconfigure the entire manufacturing process. The scale free perfused model is modular and avoids the use of a larger bioreactor with the necessity to accommodate the differing conditions and operations at larger scale. The modularity of the peripheral perfused bioreactors enables early detection of process deviation and contamination, and easy and efficient segregation or restart of an affected peripheral bioreactor. Human intervention may therefore be limited to connecting or disconnecting fluid conduits to couple the different components of the bioreactor system. The real-time control of perfusion greatly reduces or eliminates the need for human intervention on the culture, which potentially reduces the risk of contamination. Each peripheral bioreactor has substantially the same footprint, substantially the same design and substantially equal minimum and maximum working volumes. Conventional control of perfusion bioreactors, based on infrequent daily sampling and estimation of the live cell concentration, can therefore lead to large process deviations. In contrast, tight control of the perfusion or concentrate addition rate using real-time online cell concentration measurements allows bioreactors to be operated under optimum conditions for optimized manufacturing conditions. The feeder as the peripheral bioreactor independently is operated to grow and maintain the cell culture in one or more sequential operational states including, but not limited to, one or more of: batch, fed-batch, perfused batch, perfused fed-batch, and continuous perfusion states. Portions of the cell culture from the feeder are transferred to one or more of the peripheral bioreactors at one time, at multiple time points or continually based on the requirements of the peripheral bioreactors. The transfer of the culture to each bioreactor is controlled quantitatively or qualitatively using, for example, data from a capacitance probe and at-line analytical methods.

Such embodiments provide an in-vitro, continuous, universal and modular system for perfusion based on a scale out model with at least the following advantages: (i) no more scale-up; (ii) effective continuous manufacturing model; (iii) true perfusion control of the perfusion apparatus considered; (iv) limited manufacturing volume up to about 200 L; (v) same bioreactor design for process development and manufacturing; (vi) same manufacturing model for mass production; and/or (vii) production is not stopped during a contamination issue.

Materials and Methods:

Cell Line—HeLa Cells.

Media: Base SMEM Invitrogen (custom); 5% New born Calf Serum Gibco; 2 mM L-Glutamine Lonza; 1% Yeast Extract (OXOID LP0021); pH adjusted to 7-7.1 with NaHCO$_3$; Provided from a 50 L Bottle stored in a cold room at about 6° C.

Culture parameters for each bioreactor: Agitation—30 RPM; Temperature—37° C.; pH—7.1; DO—35%.

Matrix Bioreactor (Feeder)—3.6 L Applikon bioreactor. Controller type—CytoSys. Disposable acoustic perfusion—CytoPerf. VCD measurement—Online capacitance.

Culture Mode. Innoculation rate—800 ml of seed at 3×10 e6 cells/ml with 92% viability. Perfused-Batch—Volume set-point—800 ml; Trigger to switch to Perfused Fed-Batch: concentration to reach 5×10 e6 cells/ml. Perfused Fed-Batch—Concentration set-point: 5×10 e6 cells/ml; Max Volume: 2000 ml; When Max Volume reached=>Perfused-batch with a Volume Set-point at 2000 ml. Perfusion rate applied—0.33 Bioreactor Volume a day per 10 9 cells/ml real-time adjusted using on-line capacitance probe signal.

Peripheral Bioreactor 2 and 3—15 L Applikon bioreactor. Controller type—CytoSys. Disposable acoustic perfusion—CytoPerf. VCD measurement—Online capacitance.

Culture Mode. Innoculation rate—400 ml of seed at 5×10 e6 cells/ml from the Feeder; Mix with 3600 ml of fresh media pre-heated in the bioreactor. Batch Mode—Volume Set-point: 4000 ml; Trigger to switch to Fed-Batch Mode: Concentration reach 1.6×10 e6 cells/ml. Fed Batch Mode—Concentration Set-point: 1.6×10 e6 cells/ml; Trigger to harvest: Volume reach 10,000 ml.

Peripheral Bioreactor 1—15 L Applikon bioreactor. Controller type—CytoSys. Disposable acoustic perfusion—CytoPerf. VCD measurement—Online capacitance.

Culture Mode. Innoculation rate—800 ml of seed at 3×10 e6 cells/ml with 92% viability; Mix with 3600 ml of fresh media pre-heated in the bioreactor. Batch Mode—Volume Set-point: 4000 ml; Trigger to switch to Fed-Batch Mode: Concentration reach 1.6×10 e6 cells/ml. Fed Batch Mode—Concentration Set-point: 1.6×10 e6 cells/ml; Trigger to harvest: Volume reach 10,000 ml.

Results:

This example demonstrates a manufacturing process using a scale free model. The continuous perfusion method/recipe applied to the scale free model is acting remotely on the amplification process of cells as with e.g. external events (removal of cells in this case). Cells were removed multiple times, over several days to independently feed peripheral bioreactors. Once the fresh cells were transferred to the designated peripheral bioreactor, the recipe to control the process of the feeder bioreactor was switching continuously between different cultivation modes to return the feeder bioreactor as soon as possible to the targeted set-point (defined higher cell concentration of the feeder). Once the targeted cell concentration was reached again, then the feed was transferred to inoculate another designated peripheral bioreactor.

Figure 15:
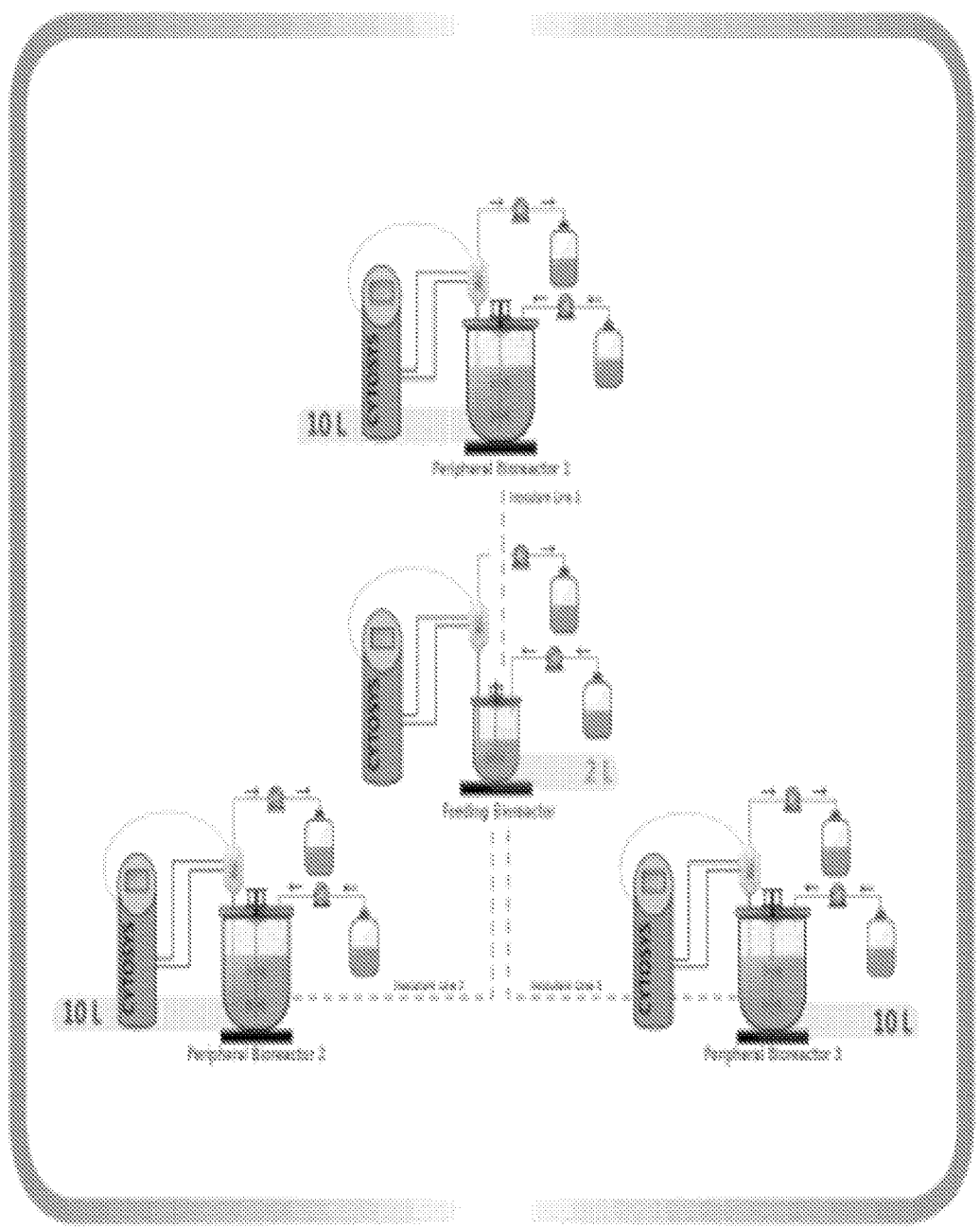
FIG. 15 is a schematic illustrating an exemplary perfusion bioreactor system of the present disclosure.
Figure 16:
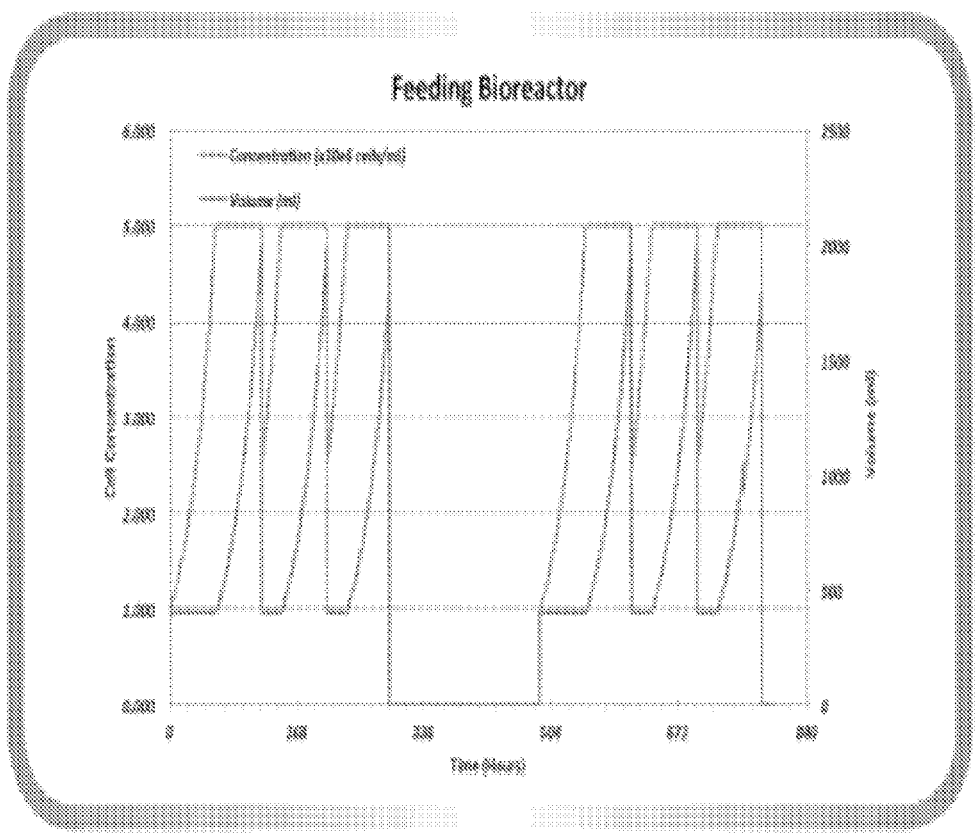
FIGS. 16-19 are graphs of cell concentration versus time for the bioreactors of FIG. 15.
Figure 17:
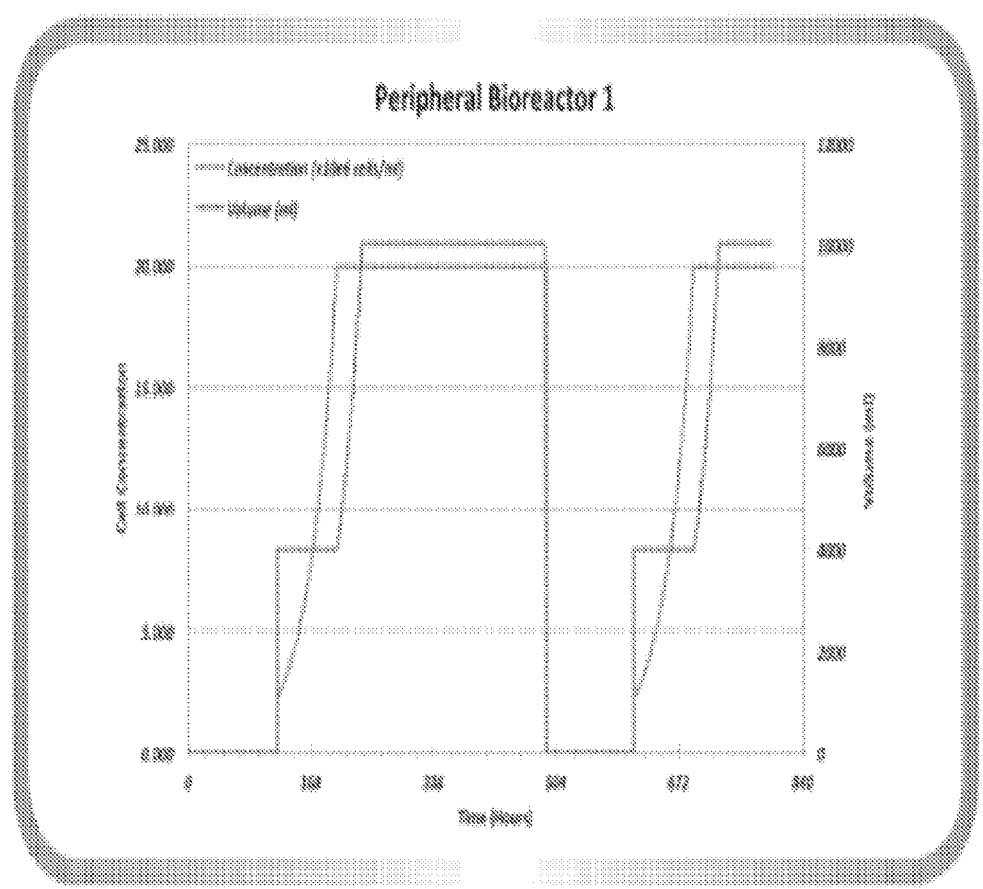
Figure 18:
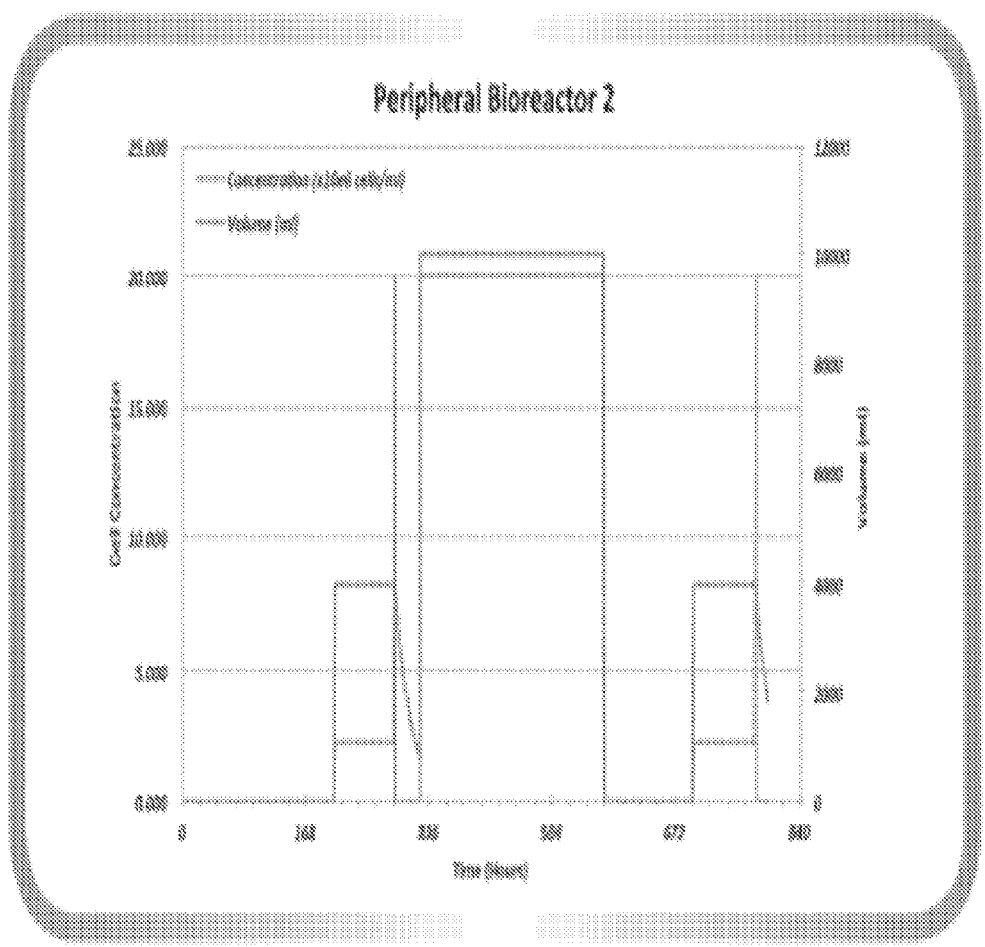
Figure 19:
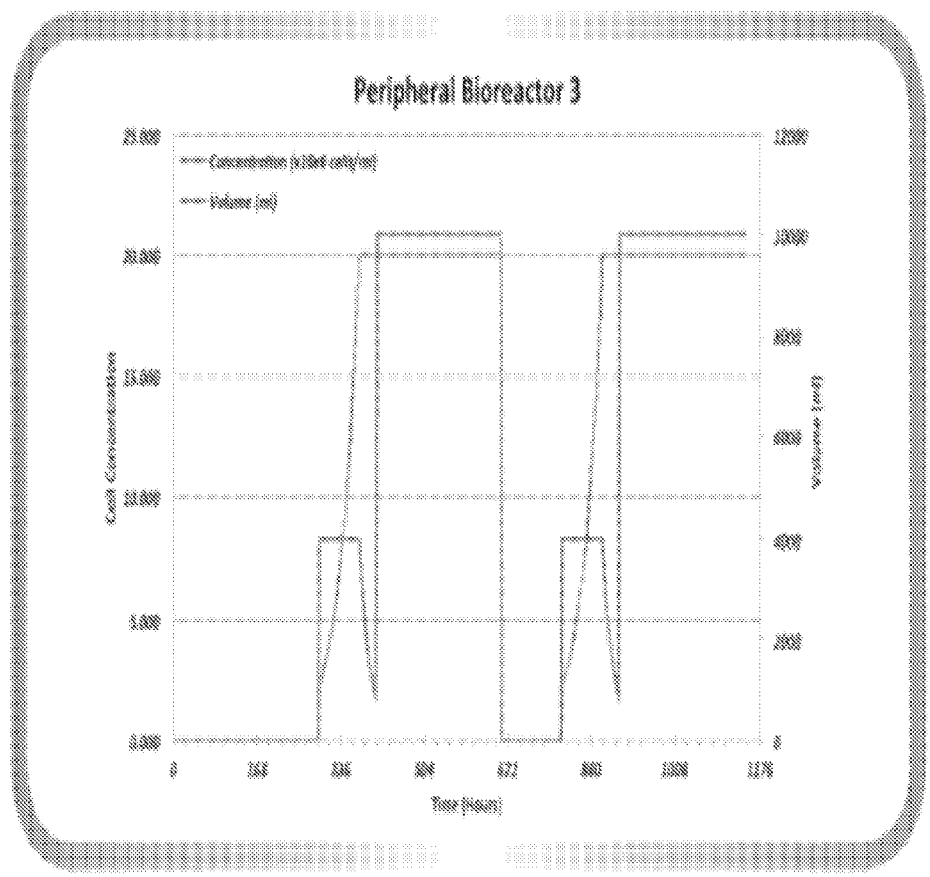

In this example of three perfused bioreactors (FIG. 15), the cell mass removed from the feeding bioreactor represents the inoculum used to feed the manufacturing stage of this process. Once the transfer is achieved then the peripheral bioreactor is switched into production mode with its own set points (which could be unique to another peripheral bioreactor, such as in a process development project).

Each peripheral bioreactor is perfused with a specific set-up and is individually controlled but managed as one control system to manage a true continuous process.

Due to the removal of fresh cells (the number of cells collected depends on the inoculum targeted), the CytoSys control of the feeder, if necessary, is safely changing how the culture is operated to return quickly to an established concentration of 5×10e6 cells/ml.

Once each peripheral bioreactor is fed with the proper amount of cells, the feeder is maintained in a dormant state (to produce only fresh cells when required) or preparing another batch of cells to inoculate the first peripheral bioreactor if culture is complete or eventually contaminated then replaced by another single-use peripheral bioreactor.

If unused, the feeder is maintained dormant in order to produce fresh cells only when needed, otherwise it can be placed in continuous mode to meet the demand for manufacturing. The whole management of the manufacturing process is a continuous production, offering from batch to batch the same quality of inoculum diverting the issue of aging when cells are maintained in such process for a long period of time.

The whole manufacturing process can be maintained for several weeks without any interruption.

The productivity and viability obtained demonstrates a significant improvement versus a traditional scale-up manufacturing with larger volumes.

CONCLUSIONS

The advantages of running the perfusion scale free method/recipe as a scale out model presents at least the following advantages: (i) Limited amount of inoculum (400 ml at 1×10 e6 cells/ml): sufficient to inoculate 3× production units; (ii) Choice of the method of perfusion device (acoustic and/or UF); (iii) Same final product from batch to batch; (iv) Similar culture model for manufacturing as Process Development; (v) Continuous process offering similar productivity at smaller scale; (vi) No qualification and validation of multiple bioreactor at different scales; (vii) Limited human intervention limiting potential contamination and extra work during non-business hours; (viii) A technical or biological process deviation with peripheral bioreactor can be isolated without perturbing the whole process; (ix) Depending on the overall productivity targeted, the feeder can inoculate 1 to x peripheral bioreactors and peripheral bioreactors can stay in stand-by mode if needed; (x) Production is managed with fresh cells with a controlled renewal of the inoculum of the feeder; and/or (xi) Flexible model for manufacturing mAbs, biomass, vaccines, virus using fed-batch and various perfusion technologies (e.g., acoustic, ATF, TFF).

Although the systems and methods of the present disclosure have been described with reference to exemplary embodiments thereof, the present disclosure is not limited to such exemplary embodiments and/or implementations. Rather, the systems and methods of the present disclosure are susceptible to many implementations and applications, as will be readily apparent to persons skilled in the art from the disclosure hereof. The present disclosure expressly encompasses such modifications, enhancements and/or variations of the disclosed embodiments. Since many changes could be made in the above construction and many widely different embodiments of this disclosure could be made without departing from the scope thereof, it is intended that all matter contained in the drawings and specification shall be interpreted as illustrative and not in a limiting sense. Additional modifications, changes, and substitutions are intended in the foregoing disclosure. Accordingly, it is appropriate that the appended claims be construed broadly and in a manner consistent with the scope of the disclosure.

What is claimed is:

1. A distributed bioreactor system for producing and maintaining a continuous biological cell culture, the system comprising:
    a nurse perfused bioreactor configured to produce and maintain a cell culture, the nurse perfused bioreactor coupled to a nurse perfusion device;
    a plurality of peripheral bioreactors configured to produce and maintain a cell culture in parallel;
    an individual and distinct peripheral perfusion device positioned proximal to and coupled to each respective individual and distinct peripheral bioreactor of the plurality of peripheral bioreactors;
    one or more control devices coupled to and configured to control the nurse perfusion device and the peripheral perfusion devices;
    a multi-way manifold coupled to the nurse perfused bioreactor; and
    a plurality of one-way fluid conduits configured to provide fluid communication from the nurse perfused bioreactor to the plurality of peripheral bioreactors, each one-way fluid conduit coupling the nurse perfused bioreactor to one of the peripheral bioreactors using the multi-way manifold;
    wherein configuration of the multi-way manifold and the one-way fluid conduits enables transfer of the cell culture from the nurse bioreactor to at least two of the peripheral bioreactors and maintains fluid isolation among each of the peripheral bioreactors.

2. The distributed bioreactor system of claim 1, wherein each peripheral bioreactor and its corresponding one-way fluid conduit are pre-assembled to form a sterile modular unit suitable for coupling to the nurse bioreactor via the multi-way manifold to scale up a volume of the cell culture of the distributed bioreactor system; optionally
    wherein each peripheral bioreactor has the same working volume;
    wherein the plurality of peripheral bioreactors comprises 3, 4 or 5 peripheral bioreactors;
    wherein the one or more control devices are configured to independently control one or more operational characteristics of the bioreactors, wherein the operational characteristics are selected from the group comprising a rate of agitation, a temperature, a pH, an oxygen level, a viable cell density based on a cell concentration measurement, a rate of perfusion, a weight, a volume, a metabolic flux, a metabolic rate, and combinations thereof; and/or
    wherein the multi-way manifold is switchable among the plurality of one-way fluid conduits, the system further comprising a manifold control device configured to activate the multi-way manifold to sequentially feed cells in the cell culture from the nurse bioreactor to at least two of the peripheral bioreactors; and/or wherein the manifold control device configures the multi-way manifold to automatically close off fluid communication between the multi-way manifold and a first peripheral bioreactor upon detecting a process deviation or a contamination in the first peripheral bioreactor.

3. The distributed bioreactor system of claim 1, further comprising:
    a plurality of cell concentration probes coupled to and configured to measure capacitance of the cell cultures of the nurse and peripheral bioreactors; and
    a plurality of volume sensing probes coupled to and configured to measure a volume, a liquid level or a liquid weight of the cell cultures of the nurse and peripheral bioreactors;
    wherein the one or more control devices are configured to control in real-time an operational state of a first bioreactor among the nurse and peripheral bioreactors based at least on a first cell concentration based on the first cell concentration measured by a first capacitance probe or other cell concentration sensors coupled to the first bioreactor and/or based on a first volume, a first liquid level or a first liquid weight measured by a first volume sensing probe coupled to the first bioreactor; optionally
    wherein the one or more control devices are configured to:
    upon inoculation of the cell culture in the first bioreactor, shut off a medium inlet port and a medium outlet port of the first bioreactor to maintain the cell culture in the first bioreactor at a substantially constant volume during a batch state;
    upon determining that a cell concentration of the cell culture in the first bioreactor has reached a first predefined cell concentration threshold, open the medium inlet port to introduce a cell growth medium into the first bioreactor to maintain the cell concentration substantially at the first cell concentration threshold during a fed-batch state;
    upon determining that a volume of the cell culture in the first bioreactor has reached a first predefined volume threshold, open the medium inlet port and the medium outlet port to control the first perfusion device to retain cells within the bioreactor, introduce the cell growth medium into the first bioreactor and release spent cell growth medium from the first bioreactor, while maintaining the volume of the cell culture substantially at the first volume threshold during a perfused batch state;
    upon determining that a cell concentration of the cell culture in the first bioreactor has reached a second predefined cell concentration threshold, open the medium inlet port and control the first perfusion device to retain cells within the bioreactor, introduce the cell growth medium into the first bioreactor and release spent cell growth medium from the first bioreactor to maintain the cell concentration substantially at the second cell concentration threshold during a perfused fed-batch state; and
    upon determining that a volume of the cell culture in the first bioreactor has reached a second predefined volume threshold, open the medium inlet port and the medium outlet port and control the first perfusion device to retain cells within the bioreactor, introduce the cell growth medium into the first bioreactor and release spent medium from the first bioreactor to maintain a volume of the cell culture substantially at the second volume threshold while maintaining the cell concentration constant or not using a bleeding of cells.

4. The distributed bioreactor system of claim 1, further comprising:
a plurality of cell concentration probes coupled to and configured to measure cell concentration of the cell cultures of the nurse and peripheral bioreactors;
wherein the one or more control devices are configured to automatically control in real-time an operational state of a first bioreactor among the nurse and peripheral bioreactors based at least on a first cell concentration based on the first cell concentration measured by a first cell concentration probe coupled to the first bioreactor; optionally
wherein the one or more control devices are configured to automatically change a first operational state of the first bioreactor to a second operational state when the first cell concentration reaches a first predefined cell concentration threshold.

5. The distributed bioreactor system of claim 4, wherein the first operational state is a batch state in which the cell concentration of the cell culture increases while the volume is maintained at a substantially constant level; and
wherein the second operational state is a fed-batch state in which the volume of the biological cell culture is adjusted to maintain the cell concentration at a substantially constant level.

6. The distributed bioreactor system of claim 4, wherein the first operational state is a perfused batch state in which a first perfusion device is operated to retain cells within the bioreactor, introduce a cell growth medium into the first bioreactor and remove spent medium from the first bioreactor, while maintaining the volume of the cell culture at a substantially constant level; and
wherein the second operational state is a perfused fed-batch state in which the first perfusion device is operated to retain cells within the bioreactor, introduce a cell growth medium into the first bioreactor and remove spent medium from the first bioreactor, while adjusting the volume of the cell culture to maintain the cell concentration at a substantially constant level.

7. The distributed bioreactor system of claim 1, further comprising:
a plurality of volume sensing probes coupled to and configured to measure a volume, a liquid level or a liquid weight of the cell cultures of the nurse and peripheral bioreactors;
wherein the one or more control devices are configured to automatically control in real-time an operational state of a first bioreactor among the nurse and peripheral bioreactors based at least on a first volume, a first liquid level or a first liquid weight indicated by a first volume sensing probe coupled to the first bioreactor; optionally
wherein the one or more control devices are configured to automatically change a first operational state of the first bioreactor to a second operational state based on the first volume, the first liquid level or a first liquid weight satisfying a first predefined volume threshold.

8. The distributed bioreactor system of claim 7, wherein the first operational state is a fed-batch state in which the volume of the biological cell culture is adjusted to maintain the cell concentration at a substantially constant level; and
wherein the second operational state is a perfused batch step in which a first perfusion device is operated to retain cells within the bioreactor, introduce a cell growth medium into the first bioreactor and remove spent medium from the first bioreactor, while maintaining the volume of the cell culture at a substantially constant level.

9. The distributed bioreactor system of claim 7, wherein the first operational state is a perfused fed-batch state in which the first perfusion device is operated to retain cells within the bioreactor, introduce a cell growth medium into the first bioreactor and remove spent medium from the first bioreactor, while adjusting the volume of the cell culture to maintain the cell concentration at a substantially constant level; and
wherein the second operational state is a cytostat state in which the first perfusion device is operated to retain cells within the bioreactor, introduce a cell growth medium into the first bioreactor and remove spent medium from the first bioreactor, while maintaining the volume of the biological cell culture at a substantially constant level.

10. The distributed bioreactor of claim 9, wherein, in the cytostat state, cells are removed from the cell culture to maintain the cell concentration at a substantially constant level.

11. The distributed bioreactor of claim 9, wherein, in the cytostat state, cells are not removed from the cell culture.

12. The distributed bioreactor system of claim 1, wherein the nurse bioreactor has a working volume of about 5 liters to about 20 liters, and each of the peripheral bioreactors has a working volume of about 20 liters to about 200 liters; and optionally
further comprising a cell bank coupled to the nurse bioreactor for inoculating the nurse bioreactor;
wherein the cell culture produces a targeted recombinant protein, optionally, an antibody; and/or
wherein the biological cell culture is maintained continuously for more than one month.

13. The distributed bioreactor system of claim 1, wherein one peripheral bioreactor is a second nurse perfused bioreactor configured to produce and maintain a cell culture, the second nurse perfused bioreactor coupled to a corresponding perfusion device;
a second plurality of peripheral bioreactors configured to produce and maintain a cell culture in parallel, each of the peripheral bioreactors of the second plurality configured to be coupled to a corresponding perfusion device;
one or more control devices coupled to and configured to control the perfusion devices associated with the second nurse and peripheral bioreactors of the second plurality;
a second multi-way manifold coupled to the second nurse perfused bioreactor; and
a plurality of one-way fluid conduits configured to provide fluid communication from the second nurse perfused bioreactor to the second plurality of bioreactors, each one-way fluid conduit coupling the second nurse perfused bioreactor to one of the peripheral bioreactors of the second plurality using the second multi-way manifold;
wherein configuration of the second multi-way manifold and the one-way fluid conduits enables transfer of the cell culture from the second nurse bioreactor to at least two of the peripheral bioreactors of the second plurality and maintains fluid isolation among each of the peripheral bioreactors of the second plurality.

14. A distributed bioreactor system for producing and maintaining a continuous biological cell culture, the system comprising:
a nurse perfused bioreactor configured to produce and maintain a cell culture, the nurse perfused bioreactor coupled to a perfusion device;
a plurality of peripheral bioreactors configured to produce and maintain a cell culture in parallel, each of the peripheral bioreactors configured to be coupled to a corresponding perfusion device;
one or more control devices coupled to and configured to control the perfusion devices associated with the nurse and peripheral bioreactors;
a multi-way manifold coupled to the nurse perfused bioreactor;
a plurality of one-way fluid conduits configured to provide fluid communication from the nurse perfused bioreactor to the plurality of bioreactors, each one-way fluid conduit coupling the nurse perfused bioreactor to one of the peripheral bioreactors using the multi-way manifold;
a disposable cell bank configured to store a collection of cells; and
a front-end perfused bioreactor configured to produce and maintain a preliminary cell culture, the front-end bioreactor coupled to the cell bank to receive at least part of the collection of cells, the front-end bioreactor coupled to the nurse bioreactor to feed the preliminary cell culture into the nurse bioreactor;
wherein configuration of the multi-way manifold and the one-way fluid conduits enables transfer of the cell culture from the nurse bioreactor to at least two of the peripheral bioreactors and maintains fluid isolation among each of the peripheral bioreactors; and
wherein the front-end bioreactor is a disposable perfused bioreactor that comprises a disposable perfusion device, and/or the front-end bioreactor is a bag device or single-use bioreactor.

15. A distributed bioreactor system for producing and maintaining a continuous biological product, the system comprising:
a nurse perfused bioreactor configured to produce and maintain a cell culture, the nurse perfused bioreactor coupled to a nurse perfusion device;
a plurality of peripheral bioreactors, each peripheral bioreactor of the plurality of peripheral bioreactors configured to: (i) perform a distinct and sequential step to the cell culture for producing and maintaining the continuous biological product, and (ii) implement a specific cell culture condition to the cell culture, the cell culture condition in each peripheral bioreactor different than the cell culture condition in the nurse perfused bioreactor;
an individual and distinct peripheral perfusion device positioned proximal to and coupled to each respective individual and distinct peripheral bioreactor of the plurality of peripheral bioreactors;
one or more control devices coupled to the nurse perfusion device and the peripheral perfusion devices, each control device configured to control the cell culture condition in the nurse perfused bioreactor and the cell culture condition in each peripheral bioreactor of the plurality of peripheral bioreactors;
a multi-way manifold coupled to the nurse perfused bioreactor; and
a plurality of one-way fluid conduits providing fluid communication from the nurse perfused bioreactor to the plurality of peripheral bioreactors, each one-way fluid conduit coupling the nurse perfused bioreactor to one of the peripheral bioreactors using the multi-way manifold, each one-way fluid conduit including a valve allowing fluid to flow from the nurse perfused bioreactor to a respectively coupled peripheral bioreactor and preventing fluid to flow from the respectively coupled peripheral bioreactor to the nurse perfused bioreactor;
wherein configuration of the multi-way manifold and the one-way fluid conduits enables transfer of the cell culture from the nurse bioreactor to at least two of the peripheral bioreactors and maintains fluid isolation among each of the peripheral bioreactors.

16. The distributed bioreactor system of claim 15, wherein the one or more control devices are configured to independently control one or more operational characteristics of the nurse perfused bioreactor and independently control one or more operational characteristics of each peripheral bioreactor of the plurality of peripheral bioreactors, wherein the operational characteristics are selected from the group consisting of a rate of agitation, a temperature, a pH, an oxygen level, a viable cell density based on a cell concentration measurement, a rate of perfusion, a weight, a volume, a metabolic flux, a metabolic rate, and combinations thereof; and
wherein the multi-way manifold is switchable among the plurality of one-way fluid conduits, the system further including a manifold control device configured to activate the multi-way manifold to sequentially feed cells in the cell culture from the nurse bioreactor to at least two of the peripheral bioreactors, the manifold control device controlling fluid flow rates at the multi-way manifold.

* * * * *